United States Patent

Hamprecht et al.

[11] Patent Number: 5,849,920
[45] Date of Patent: Dec. 15, 1998

[54] SUBSTITUTED TRIFLUOROMETHYLPYRIDINES

[75] Inventors: Gerhard Hamprecht, Weinheim; Elisabeth Heistracher, Mannheim; Ralf Klintz, Grünstadt; Peter Schäfer, Ottersheim; Cyrill Zagar, Ludwigshafen, all of Germany

[73] Assignee: BASF Aktiengesellschaft, Ludwigshafen, Germany

[21] Appl. No.: 891,967

[22] Filed: Jul. 14, 1997

Related U.S. Application Data

[62] Division of Ser. No. 695,475, Aug. 12, 1996, Pat. No. 5,750,705.

[30] Foreign Application Priority Data

Aug. 21, 1995 [DE] Germany .................. 195 30 605.8

[51] Int. Cl.$^6$ .................. A01N 43/40; C07D 213/77; C07D 401/04; C07D 213/82
[52] U.S. Cl. .................. 546/268.1; 504/244; 546/275.4; 546/300; 546/303
[58] Field of Search ................ 546/268.1, 292, 546/300, 303

[56] References Cited

U.S. PATENT DOCUMENTS

| | | | |
|---|---|---|---|
| 4,563,530 | 1/1986 | Fujioka et al. | 646/345 |
| 4,772,312 | 9/1988 | Schallner et al. | 504/253 |
| 5,156,656 | 10/1992 | Parker et al. | 95/53 |
| 5,167,691 | 12/1992 | Maravetz | 504/282 |

*Primary Examiner*—Alan L. Rotman
*Attorney, Agent, or Firm*—Keil & Weinkauf

[57] ABSTRACT

A trifluoromethylpyridine of the formula Ib

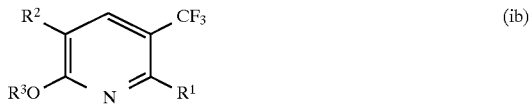

where the substituents have the following meanings:

$R^1$ is chlorine or fluorine;
$R^2$ is halogen; and
$R^3$ is $C_1$–$C_6$-alkyl, $C_2$–$C_6$-alkenyl or $C_2$–$C_6$-alkynyl, said groups being optionally substituted with 1 to 6 halogen atoms, $C_3$–$C_6$-cycloalkyl which is optionally substituted with 1 to 3 $C_1$–$C_3$-alkyl radicals, $C_1$–$C_6$-cyanoalkyl, $C_1$–$C_4$-alkoxy-$C_2$–$C_6$-alkyl, 3-oxetanyl, carboxyl-$C_1$–$C_6$-alkyl, $C_1$–$C_6$-alkoxycarbonyl-$C_1$–$C_6$-alkyl, $C_1$–$C_4$-alkoxy-$C_2$–$C_4$-alkoxycarbonyl-$C_1$–$C_6$-alkyl, aminocarbonyl-$C_1$–$C_6$-alkyl, $C_1$–$C_4$-alkylaminocarbonyl-$C_1$–$C_6$-alkyl, $C_1$–$C_4$-dialkylaminocarbonyl-$C_1$–$C_6$-alkyl, $C_2$–$C_4$-alkenylaminocarbonyl-$C_1$–$C_6$-alkyl, $C_3$–$C_4$-alkynylaminocarbonyl-$C_1$–$C_6$-alkyl, $C_1$–$C_4$-alkyl-$C_3$–$C_4$-alkenylaminocarbonyl-$C_1$–$C_6$-alkyl, $C_1$–$C_4$-alkyl-$C_3$–$C_4$-alkynylaminocarbonyl-$C_1$–$C_6$-alkyl, $C_3$–$C_6$-($\alpha$-alkylalkylidene)iminoxy-$C_2$–$C_6$-alkyl, cyclopropylmethyl, $C_1$–$C_6$-alkylamino, $C_1$–$C_6$-dialkylamino, $C_1$–$C_6$-alkylideneimino or $\alpha$-($C_1$–$C_4$-alkyl)-$C_2$–$C_6$-alkylideneimino; and
halogen is fluorine, chlorine, bromine or iodine.

11 Claims, No Drawings

SUBSTITUTED TRIFLUOROMETHYLPYRIDINES

This is a divisional of application Ser. No. 08/695,475, filed Aug. 12, 1996, now U.S. Pat. No. 5,750,705.

The invention relates to novel substituted trifluoromethylpyridines of the general formula Ia or Ib

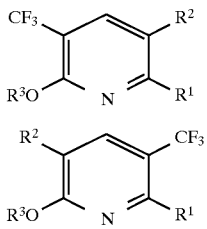

where the substituents have the following meanings:

$R^1$ is amino or hydrazino, in the case of Ib additionally chlorine or fluorine;

$R^2$ is halogen; and $R^3$ is $C_1$–$C_6$-alkyl, $C_2$–$C_6$-alkenyl or $C_2$–$C_6$-alkynyl, it being possible for these groups to have attached to them up to 6 halogen atoms, $C_3$–$C_6$-cycloalkyl which can have attached to it up to 3 $C_1$–$C_3$-alkyl radicals, $C_1$–$C_6$-cyanoalkyl, $C_1$–$C_4$-alkoxy-$C_2$–$C_6$-alkyl, 3-oxetanyl, carboxyl-$C_1$–$C_6$-alkyl, $C_1$–$C_6$-alkoxycarbonyl-$C_1$–$C_6$-alkyl, $C_1$–$C_4$-alkoxy-$C_2$–$C_4$-alkoxycarbonyl-$C_1$–$C_6$-alkyl, aminocarbonyl-$C_1$–$C_6$-alkyl, $C_1$–$C_4$-alkylaminocarbonyl-$C_1$–$C_6$-alkyl, $C_1$–$C_4$-dialkylaminocarbonyl-$C_1$–$C_6$-alkyl, $C_2$–$C_4$-alkenylaminocarbonyl-$C_1$–$C_6$-alkyl, $C_3$–$C_4$-alkynylaminocarbonyl-$C_1$–$C_6$-alkyl, $C_1$–$C_4$-alkyl-$C_3$–$C_4$-alkenylaminocarbonyl-$C_1$–$C_6$-alkyl, $C_1$–$C_4$-alkyl-$C_3$–$C_4$-alkynylaminocarbonyl-$C_1$–$C_6$-alkyl, $C_3$–$C_6$-($\alpha$-alkylalkylidene)iminoxy-$C_2$–$C_6$-alkyl, cyclopropylmethyl, $C_1$–$C_6$-alkyl-amino, $C_1$–$C_6$-dialkylamino, $C_1$–$C_6$-alkylideneimino- or $\alpha$-($C_1$–$C_4$-alkyl)-$C_2$–$C_6$-alkylideneimino; and halogen is fluorine, chlorine, bromine or iodine.

The invention furthermore relates to a process for the preparation of the trifluoromethylpyridines Ia or Ib by reacting 2,3,6-trihalo-5-trifluoromethylpyridines with ammonia or hydrazine and alcohols or vice versa, first with alcohols and then with ammonia or hydrazine, and to novel 2-fluoro- or 2-chloro-3-trifluoromethyl-5-halo-6-oxy-substituted pyridines Ib.

The invention furthermore relates to a process for the preparation of 3-chloro-2,6-difluoro-5-trifluoromethylpyridine III from 2,3,6-trichloro-5-trifluoromethylpyridine II by means of a halogen exchange reaction.

The invention furthermore relates to a process for the preparation of 5-chloro-2-fluoro-3-trifluoromethyl-6-oxy-substituted pyridines VI from the 2,5-dichloro-3-trifluoromethyl-6-oxy-substituted pyridines VII by means of a halogen exchange reaction.

2-Amino- or 2-hydrazinopyridines are valuable intermediates for organic syntheses, in particular for the preparation of crop protection products, for example herbicidally active 1-pyridylyrazole derivatives.

While 2-amino-3,6-dichloro-5-trifluoromethylpyridine has been disclosed for some time (U.S. Pat. No. 4,349,681), reaction products which are derived from the corresponding 6-chloropyridine derivative by a nucleophilic reaction of alcohols or salts thereof have not been described to date. In in-house experiments, it has been found that, for example, 2-amino-3,6-dichloro-5-trifluoromethylpyridine does not react with sodium methylate under reflux and that the 5-$CF_3$ group is preferentially hydrolyzed to the corresponding methyl carboxylate when potassium hydroxide is present. Traces of 2-amino-3-chloro-6-methoxy-5-trifluoromethylpyridine, besides several impurities, were only detected in a specific solvent mixture with DMF after heating for 90 hours. However, the yield is unsatisfactory at 5%.

If, in contrast, the novel 2,5-dichloro-6-methoxy-3-trifluoromethylpyridine is reacted with ammonia, the undesired 2-amino-3,6-dichloro-5-trifluoromethylpyridine is predominantly formed while the methoxy group is lost.

Given this background, it is easy to understand that 2,6-(or 6,2-)alkoxy, -amino- (or -hydrazino-) halotrifluoromethylpyridines have not been disclosed to date.

We have now found that the novel trifluoromethylpyridines of the general formula Ia or Ib

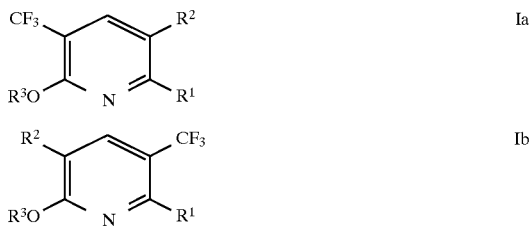

where the substituents have the following meanings:

$R^1$ is amino or hydrazino, in the case of Ib additionally chlorine or fluorine;

$R^2$ is halogen; and $R^3$ is $C_1$–$C_6$-alkyl, $C_2$–$C_6$-alkenyl or $C_2$–$C_6$-alkynyl, it being possible for these groups to have attached to them up to 6 halogen atoms, $C_3$–$C_6$-cycloalkyl which for its part can have attached to it up to 3 $C_1$–$C_3$-alkyl radicals, $C_1$–$C_6$-cyanoalkyl, $C_1$–$C_4$-alkoxy-$C_2$–$C_6$-alkyl, 3-oxetanyl, carboxyl-$C_1$–$C_6$-alkyl, $C_1$–$C_6$-alkoxycarbonyl-$C_1$–$C_6$-alkyl, $C_1$–$C_4$-alkoxy-$C_2$–$C_4$-alkoxycarbonyl-$C_1$–$C_6$-alkyl, $C_1$–$C_4$-alkylaminocarbonyl-$C_1$–$C_6$-alkyl, aminocarbonyl-$C_1$–$C_6$-alkyl, $C_1$–$C_4$-dialkylaminocarbonyl-$C_1$–$C_6$-alkyl, $C_2$–$C_4$-alkenylaminocarbonyl-$C_1$–$C_6$-alkyl, $C_3$–$C_4$-alkynylaminocarbonyl-$C_1$–$C_6$-alkyl, $C_1$–$C_4$-alkyl-$C_3$–$C_4$-alkenylaminocarbonyl-$C_1$–$C_6$-alkyl, $C_1$–$C_4$-alkyl-$C_3$–$C_4$-alkynylaminocarbonyl-$C_1$–$C_6$-alkyl, $C_3$–$C_6$-($\alpha$-alkylalkylidene)iminoxy-$C_2$–$C_6$-alkyl, cyclopropylmethyl, $C_1$–$C_6$-alkyl-amino, $C_1$–$C_6$-dialkylamino, $C_1$–$C_6$-alkylideneimino- or $\alpha$-($C_1$–$C_4$-alkyl)-$C_2$–$C_6$-alkylideneimino; and halogen is fluorine, chlorine, bromine or iodine, are obtained advantageously when 2,3,6-trichloro-5-trifluoromethylpyridine, of the formula II,

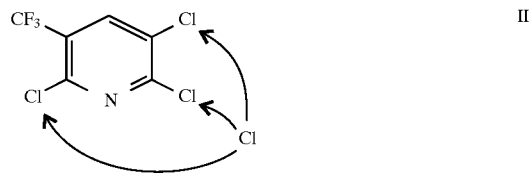

is subjected, in a first step, to a halogen exchange reaction to give the corresponding 3-chloro-2,6-difluoro-5-trifluoromethylpyridine, of the formula III,

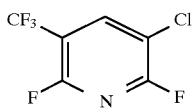

and this is then reacted in succession with ammonia or hydrazine to give 2-amino- or 2-hydrazino-3-chloro-6-fluoro-5-trifluoromethylpyridine, of the formula IV or IV',

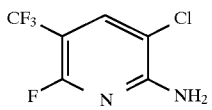

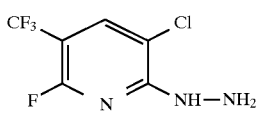

and the product is finally reacted with an alcohol of the formula V

where $R^3$ has the abovementioned meaning, or with an alkali metal salt or alkaline earth metal salt thereof, to give the compounds of the formula Ia, or when, to synthesize the compounds of the formula Ib, the above 3-chloro-2,6-difluoro-5-trifluoromethylpyridine, of the formula III,

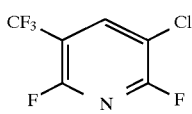

is reacted in succession first with an alcohol of the formula V

where $R^3$ has the abovementioned meaning, or with an alkali metal salt or alkaline earth metal salt thereof, to give the compounds of the formula VI

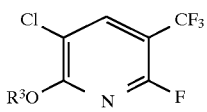

and the product is finally reacted with ammonia or hydrazine.

Furthermore, it has been found that the compounds of the formula Ib can also be obtained by first reacting 2,3,6-trichloro-5-trifluoromethylpyridine, of the formula II,

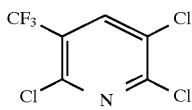

with an alcohol of the formula V

where $R^3$ has the abovementioned meaning to give the compounds of the formula VII

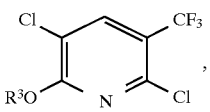

then subjecting these compounds to a halogen exchange reaction to give the compounds of the formula VI

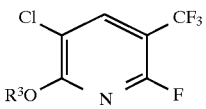

where $R^3$ has the abovementioned meaning, and finally reacting these compounds with ammonia or hydrazine as described above to give the end products Ib.

Furthermore it has been found in the case of the synthesis of the 2-alkoxy-3-chloro-6-hydrazino-5-trifluoromethylpyridines and of their unsaturated analogs as other representatives of the end products Ib that they can also be obtained by reacting the compounds of the formula VII

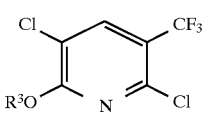

where $R^3$ has the abovementioned meaning directly with hydrazine without first carrying out a halogen exchange reaction.

When in the case of the synthesis of the compounds Ia, 2,3,6-trichloro-5-trifluoromethylpyridine, potassium fluoride as halogen exchange reagent and the nucleophiles ammonia and methanol are used, the reaction can be described by the equation below:

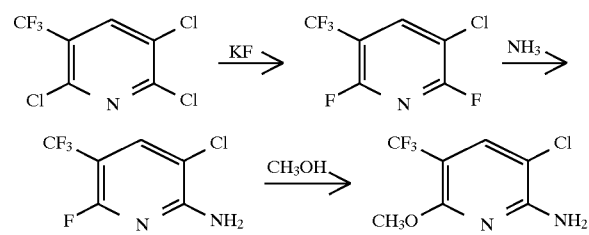

If hydrazine is used in place of ammonia, the reaction proceeds in a similar manner following the equation below:

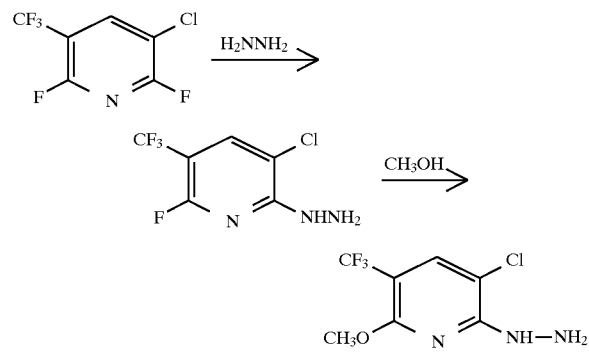

In the case of the synthesis of the compounds Ib, the reaction is also based on 3-chloro-2,6-difluoro-5-trifluoromethylpyridine III using, for example, methanol and ammonia, following the equation below:

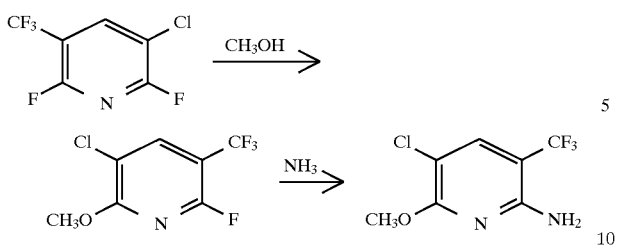

If, in place of ammonia, hydrazine is used, analogous compounds Ib are obtained following the equation below:

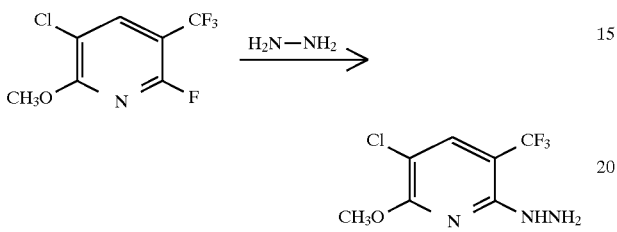

To synthesize the compounds Ib, it is alternatively also possible to start from 2,3,6-trichloro-5-trifluoromethylpyridine II and, for example, propargyl alcohol, then to carry out a halogen exchange reaction and finally to react the product with ammonia following the equation below:

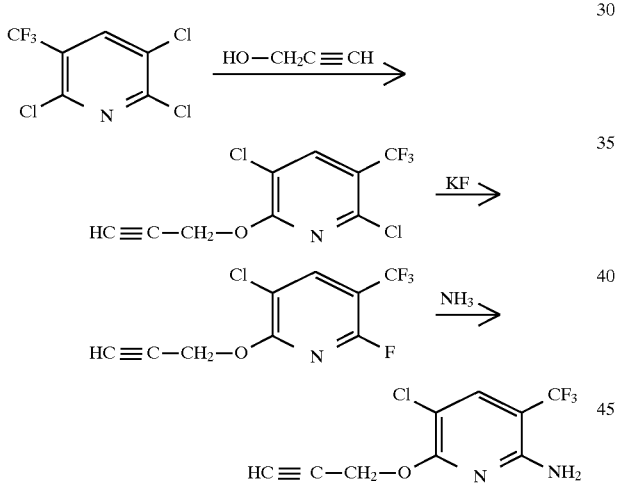

If hydrazine is used in place of ammonia, the analogous compounds Ib result following this equation.

The process gives novel 2-amino- or 2-hydrazinohalotrifluoromethylpyridines in high yield and high purity via a simple and economical route. Contrary to expectation, the trifluoromethyl group is not hydrolyzed, nor is an alkoxy group which has already been introduced eliminated again by ammonia. With a view to the prior art, all these advantageous properties are surprising. The meanings mentioned above for the substituent $R^3$ in formulae Ia and Ib represent collective terms for individual enumerations of the individual group members. All carbon chains, ie. all alkyl, alkenyl, alkynyl, haloalkyl, haloalkenyl, haloalkynyl and haloalkoxy moieties, can be straight-chain or branched. Halogenated substituents preferably have attached to them 1–6 identical or different halogen atoms.

Examples of individual meanings are:
halogen: fluorine, chlorine, bromine and iodine, preferably fluorine and chlorine;

$C_1$–$C_4$-alkyl: methyl, ethyl, n-propyl, 1-methylethyl, n-butyl, 1-methylpropyl, 2-methylpropyl and 1,1-dimethylethyl;

$C_1$–$C_6$-alkyl: $C_1$–$C_4$-alkyl as mentioned above, and also n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-diamethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-2-methylpropyl;

$C_1$–$C_8$-alkyl: $C_1$–$C_6$-alkyl as mentioned above, and also n-heptyl and n-octyl, inter alia;

$C_2$–$C_4$-alkenyl: ethenyl, prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl and 2-methylprop-2-en-1-yl;

$C_3$–$C_6$-alkenyl: prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethyl-but-2-en-1-yl, 2-ethylbut-3-en-1-yl, 1,1,2-trimethylprop-2-en-1-yl, 1-ethyl-1-methyl-prop-2-en-1-yl, 1-ethyl-2-methylprop-1-en-1-yl and 1-ethyl-2-methylprop-2-en-1-yl, preferably ethenyl and prop-2-en-1-yl;

$C_2$–$C_6$-alkynyl: ethynyl and $C_3$–$C_6$-alkynyl such as prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-1-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl, preferably prop-2-yn-1-yl, 1-methylprop-2-yn-1-yl;

$C_2$–$C_6$-haloalkenyl: $C_3$–$C_6$-alkenyl as mentioned above, 1–6 hydrogen atoms in each case being replaced by fluorine, chlorine and/or bromine;

$C_2$–$C_6$-haloalkynyl: $C_2$–$C_6$-alkynyl as mentioned above, one to six hydrogen atoms in each case being replaced by fluorine, chlorine and/or bromine;

$C_3$–$C_6$-cycloalkyl: cyclopropyl, cyclobutyl, cyclopentyl and cyclohexyl, preferably cyclopropyl, cyclopentyl and cyclohexyl;

$C_1$–$C_6$-haloalkyl: $C_1$–$C_4$-alkyl as mentioned above which is partially or fully substituted by fluorine, chlorine and/or bromine, eg. chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 3-chloropropyl, preferably trifluoromethyl;

cyano($C_1$–$C_6$)alkyl: $C_1$–$C_6$-alkyl as mentioned above where in each case one hydrogen atom is replaced by the cyano group, eg. cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl, and 2-cyanomethylprop-2-yl, preferably cyanomethyl, 1-cyano-1-methylethyl;

$C_1$–$C_4$-alkoxy: methoxy, ethoxy, n-propoxy, 1-methylethoxy, n-butoxy, 1-methylpropoxy, 2-methylpropoxy and 1,1-dimethylethoxy, preferably methoxy, ethoxy and 1-methylethoxy;

$C_1$–$C_4$-alkylamino: methylamino, ethylamino, n-propylamino, 1-methylethylamino, n-butylamino, 1-methylpropylamino, 2-methylpropylamino and 1,1-dimethylethylamino, preferably methylamino and ethylamino;

di($C_1$–$C_4$-alkyl)amino: N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl) amino, N-ethyl-N- (2-methylpropyl) amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethyl-ethyl)-N-(1-methylpropyl)amino and N-(1,1-dimethylethyl)-N-(2-methylpropyl)amino, preferably dimethylamino and diethylamino;

$C_1$–$C_4$-alkylaminocarbonyl: methylaminocarbonyl, ethylaminocarbonyl, n-propylaminocarbonyl, 1-methylethylaminocarbonyl, n-butylaminocarbonyl, 1-methylpropylaminocarbonyl, 2-methylpropylaminocarbonyl and 1,1-dimethylethylaminocarbonyl, preferably methylaminocarbonyl and ethylaminocarbonyl;

di($C_1$–$C_4$-alkyl)aminocarbonyl: N,N-dimethylaminocarbonyl, N,N-diethylaminocarbonyl, N,N-dipropylaminocarbonyl, N,N-di-(1-methylethyl)aminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl and N-(1,1-dimethylethyl)-N-(2-methylpropyl)aminocarbonyl, preferably dimethylaminocarbonyl and diethylaminocarbonyl;

$C_1$–$C_6$-alkylideneimino; methylideneimino, ethylideneimino, propylideneimino, butylideneimino, pentylideneimino, hexylideneimino, preferably methylideneimino and ethylideneimino;

α-($C_1$–$C_2$-alkyl)-$C_2$–$C_4$-alkylideneimino: α-methylethylideneimino, α-methylpropylideneimino, α-ethylethylideneimino, α-ethylpropylideneimino, α-methylbutylideneimino, preferably α-methylethylideneimino and α-methylpropylideneimino.

Especially preferred amongst the compounds Ia and Ib are furthermore those where $R^1$ is amino or hydrazino, in the case of Ib additionally fluorine, $R^2$ is chlorine or fluorine, $R^3$ is $C_1$–$C_4$-alkyl, $C_2$–$C_4$-alkenyl or $C_2$–$C_4$-alkynyl, it being possible for these groups to have attached to them up to 6 halogen atoms, $C_3$–$C_6$-cycloalkyl which, in turn, can have attached to it up to 3 methyl radicals, $C_1$–$C_2$-alkoxy-$C_2$–$C_4$-alkoxycarbonyl-$C_1$–$C_4$-alkyl, $C_1$–$C_4$-cyanoalkyl, $C_1$–$C_2$-alkoxy-$C_2$–$C_4$-alkyl, 3-oxetanyl, carboxyl-$C_1$–$C_4$-alkyl, $C_1$–$C_4$-alkoxycarbonyl-$C_1$–$C_4$-alkyl, $C_1$–$C_2$-alkoxy-$C_2$–$C_4$- alkoxycarbonyl-$C_1$-$C_4$-alkyl, $C_1$-$C_2$-alkylaminocarbonyl-$C_1$-$C_4$-alkyl, $C_3$-$C_4$-($\alpha$-alkylidene)iminoxy-$C_2$-$C_4$-alkyl, cyclopropylmethyl, $C_1$-$C_4$-alkylamino, $C_1$-$C_4$-dialkylamino, $C_1$-$C_4$-alkylideneimino or $\alpha$-($C_1$-$C_2$-alkyl)-$C_2$-$C_4$-alkylideneimino.

The starting material III—3-chloro-2,6-difluoro-5-trifluoroethylpyridine—which is required for the preparation of the compounds IV is used in U.S. Pat. No. 5,156,656; however, its preparation has not been described in the literature to date.

The novel substituted pyridines Ia and Ib are accessible by various routes, preferably by one of the processes below:

The halogen exchange reaction of 2,3,6-trichloro-5-trifluoromethylpyridine II is preferably carried out with potassium fluoride at from 100°–180° C., preferably 130° to 170° C., in the presence of a polar solvent.

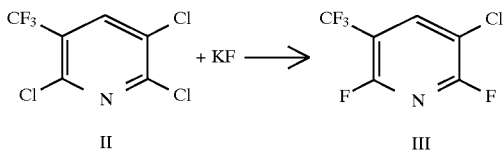

Solvents which are used for these reactions are nitrites such as acetonitrile, propionitrile, butyronitrile, isobutyronitrile, glycol ethers such as dimethyl glycol ether, diethyl glycol ether, diethylene glycol dimethyl ether, carboxamides such as DMF, N-methylpyrrolidone, ureas such as tetraethylurea, tetrabutylurea, dimethylethyleneurea, dimethylpropyleneurea, sulfoxides such as dimethyl sulfoxide and, preferably, sulfones such as dimethyl sulfone, diethyl sulfone, tetramethylene sulfone (sulfolane) or pentamethylene sulfone. The process can also be carried out according to the invention in the melt without an addition of a solvent.

The halogen exchange reaction proceeds at a high rate even without a catalyst. However, it can be accelerated by adding a catalyst, eg. a crown ether or cryptands. These substances are organic complex ligands which are particularly suitable for binding alkali. The cryptands provide three-dimensional chelation. For the preparation of these substances, see "Kontakte" ["catalysts"] (1977), pages 11–31 and 36–48. Preferred catalysts are crown ethers, of which the following compounds may be mentioned by way of example: 12-crown-4, 14-crown-4, dibenzo-14-crown-4, 18-crown-5, 18-crown-6, dibenzo-18-crown-6 or aza-18-crown-6.

These catalysts are expediently employed in an amount of 0.05–5, in particular 0.1–2, mol percent per mole of starting material II.

The molar ratios in which the starting compounds are reacted with each other are 1.9–2.8, preferably 2–2.4, for the ratio of potassium fluoride to pyridine derivative II. The concentration of the educts in the solvent is 0.1–5 mol/l, preferably 0.2–2 mol/l.

The compounds III can be prepared particularly advantageously when prior to the actual halogen exchange reaction the pyridine derivative II is treated, for example, with 0.1–0.4, expediently 0.15–0.3, mol of an acid chloride of sulfurous acid or carbonic acid at up to 150° C., expediently from 50° C. to 120° C., in particular 70°–100° C., in the presence of an aliphatic sulfone, and the reaction mixture is then reacted with potassium fluoride at 70°–250° C., preferably 80°–200° C.

Catalysts which are suitable for this process step are, for example, N,N-disubstituted carboxamides such as DMF, N,N-dimethylacetamide or N,N-diisopropylacetamide. The catalyst is expediently employed in an amount of 0.2–2 percent by weight based on the acid chloride.

When carrying out the reaction with the acid chloride, it is expedient to heat the mixture until the evolution of gas has ceased. It is recommended to remove excess acid chloride for example by passing in an inert gas such as nitrogen or by applying a vacuum.

The potassium fluoride, which has expediently been dried beforehand, is then added to this mixture, and the mixture obtained by stirring is maintained at reaction temperature for 1–10 hours.

Fluoride salts which are suitable according to the invention are, besides potassium fluoride, also tetraalkyl($C_1$-$C_{13}$) ammonium fluoride and suitable mixtures of these or with cesium fluoride or rubidium fluoride, these mixtures with cesium fluoride comprising not more than 50% by weight of cesium fluoride. Fluoride mixtures which are preferably used are those which comprise at least 75% by weight of potassium fluoride; in particular, such mixtures are composed of not less than 90% by weight of potassium fluoride and not more than 10% by weight of cesium fluoride or of 60% by weight of potassium fluoride and 40% by weight of rubidium fluoride. In a further preferred embodiment, only potassium fluoride is employed as the fluoride salt.

Phase transfer catalysts which can be used are quaternary ammonium or phosphonium salts. Suitable compounds which may be mentioned are the following: tetraalkyl ($C_1$-$C_{18}$)ammonium chlorides, bromides or fluorides, tetraalkyl($C_1$-$C_{18}$)phosphonium chlorides or bromides, tetraphenylphosphonium chloride or bromide, (phenyl)$_m$-(alkyl($C_1$-$C_{18}$))$_n$phosphonium chlorides or bromides, where m=1–3, n=3–1 and m+n=4. Mixtures of these can also be employed. A suitable choice of the catalyst for the compound to be reacted in each case, which can readily be determined by a few routine experiments, results in high space efficiencies and yields; moreover, the idle times of the equipment and the overall equipment costs are particularly favorable in the process according to the invention.

The amount of phase transfer catalyst is generally up to 20% by weight, preferably from 3 to 15% by weight, particularly preferably from 3 to 8% by weight, based on the amount of fluoride salt employed.

Phase transfer catalysts which can also be used are oligo- or polyalkylene glycol dimethyl ethers, the alkylene radical having 2–6 C atoms, preferably 2 and/or 3 C atoms, ie. preferably the ethylene and/or propylene radical, in particular only the ethylene radical. The number of the O-ethylene (glycol) units (—O—CH$_2$—CH$_2$—)$_n$ and/or of the O-propylene units in these compounds can range from n=4 (eg. tetraethylene glycol dimethyl ether) to approximately n=150; however, ethers whose degree of polymerization is between n=4 and n=25 are preferably employed. In the case of alkylene radicals having more than 3 C atoms, n is generally not greater than 6. The amount of these ethers employed, in particular of the glycol ethers, is in most cases from approximately 0.6% by weight to approximately 200% by weight, preferably from approximately 5 to approximately 100% by weight and particularly preferably from approximately 10 to approximately 50% by weight, based on the amount of the fluoride salt employed. The particular advantage when using these compounds is the fact that in most cases less solvent can be used in relation to the educt since the glycol ethers generally liquefy at the reaction temperature. Mixtures of these ethers with each other and mixtures of these ethers (singly or in the form of a mixture) with the quaternary ammonium or phosphonium salts can also be employed, preferably glycol ethers with quaternary phosphonium salts.

If tetraalkyl($C_1$–$C_{18}$)ammonium fluorides are used as the fluoride salt, an addition of another phase transfer catalyst is not necessary since the fluoride salt itself is such a phase transfer catalyst, which can thus be employed in stoichiometric and larger amounts.

While the use of spray-dried alkali metal fluoride in the process according to the invention reduces the reaction times in some cases, it is not absolutely necessary. It is also possible to carry out the process with an addition of acid binders such as alkali metal carbonates and alkaline earth metal carbonates or basic oxides, for example magnesium oxide, or suitable mixtures. Particularly preferred in this context is potassium carbonate, which is used in amounts of from approximately 1 to approximately 10% by weight, preferably from approximately 4 to approximately 6% by weight, based on the amount of fluoride salt.

The acid binders are generally not essential for the course of the reaction. In some cases, the reaction rate is reduced considerably by the formation of hydrogen fluoride during the reaction. In these cases, it is advantageous, especially for avoiding equipment corrosion, to carry out the process in the presence of such acid scavengers. The use of these compounds when fractionating the reaction mixture or the crude product can be desirable due to corrosion in the fractionating apparatus, magnesium oxide being particularly preferred for this purpose. To this end, up to approximately 10% by weight of acid scavenger are added to the fractionating still, preferably from approximately 3 to 8% by weight based on the total amount of bottom distillation product employed.

After the reaction with alkali metal fluoride, the mixture is worked up in a manner known per se, eg. by filtration, washing the solids and distillation of filtrate and washing filtrates. In the case of solvents which are miscible with water, the pyridine derivatives Ia can also be precipitated by adding water and the precipitate worked up as described above.

The 2,6-difluoropyridine III and the 2-fluoropyridines VI can be reacted with ammonia or hydrazine, or the 2,5-dichloropyridines VII can be reacted with hydrazine, in the absence or, advantageously, the presence of a solvent. Suitable solvents are in particular those listed below:

hydrocarbons, eg. pentane, hexane, heptane, cyclohexane, alcohols, eg. methanol, ethanol, n-propanol, isopropanol, butanol, isobutanol, ethers, such as methyl tert-butyl ether, diethyl ether, ethyl propyl ether, n-butyl ethyl ether, di-n-butyl ether, diisobutyl ether, diisoamyl ether, diisopropyl ether, cyclohexylmethyl ether, tetrahydrofuran, 1,2-dimethoxyethane, diethylene glycol dimethyl ether and anisole, esters such as ethyl acetate, n-butyl acetate and isobutyl acetate, chlorinated hydrocarbons such as methylene chloride, 1,1,2,2,-tetrachloroethane, 1,1-dichloroethylene, 1,2-dichloroethane, chlorobenzene, 1,2-, 1,3-, 1,4-dichlorobenzene, 1-chloro-naphthalene and 1,2,4-trichlorobenzene, nitrohydrocarbons such as nitromethane, nitroethane, nitropropane and nitrobenzene, dipolar aprotic solvents, eg. acetonitrile, propionitrile, dimethylformamide, dimethylacetamide, dimethyl sulfoxide, N-methylpyrrolidone, 1,3-dimethyltetrahydro-2-(1H)-pyrimidinone and 1,3-dimethylimidazolidin-2-one, aromatics, eg. benzene, toluene and xylene or heteroaromatics, eg. pyridine, $\alpha,\beta,\gamma$-picoline and quinoline, or water, and mixtures of these.

The solvent is expediently employed in an amount of 100–2000% by weight, preferably 400–1200% by weight, based on the starting materials III, VI or VII.

It is advantageous to add 0.9–10, in particular 1.1–5, mol equivalents of ammonia or hydrazine hydrate based on the starting materials III, VI or VII to a mixture of the starting materials III, VI or VII in the course of 0.25–2 hours in one of the abovementioned solvents at 0°–180° C., preferably 10°–130° C., and to continue stirring until the reaction is complete (approximately 2–20 hours).

If only approximately stoichiometric amounts of ammonia or hydrazine are employed, it is expedient additionally to use an organic auxiliary base to scavenge the hydrogen halide which forms. Suitable auxiliary bases are customary organic bases such as trimethylamine, triethylamine, N-ethyldiisopropylamine, triisopropylamine, N,N-dimethylaniline, N,N-dimethylcyclohexylamine, N-methylpyrrolidine, pyridine, quinoline, $\alpha,\beta,\gamma$-picoline, 2,4- and 2,6-lutidine and triethylenediamine. However, it is also possible to use inorganic basic substances as auxiliary base, for example an alkali metal hydroxide or alkaline earth metal hydroxide such as lithium hydroxide, sodium hydroxide, potassium hydroxide, calcium hydroxide, magnesium hydroxide or zinc hydroxide, or an alkali metal hydrogen carbonate, alkali metal carbonate, alkaline earth metal hydrogen carbonate or alkaline earth metal carbonate of the same cations as mentioned above. In general, additions of 0.9–1.1 equivalents of auxiliary base based on the starting materials III, VI or VII will suffice.

The reaction can be carried out under atmospheric pressure or under elevated pressure, continuously or batchwise.

Working-up can be carried out in the customary manner, for example the reaction mixture is extracted with water to remove the salts, and the organic phase is dried and purified, for example by chromatography or distillation. However, it is also possible to concentrate the organic phase directly and to stir the residue with a solvent.

The 2,6-dichloropyridines II, the 2,6-difluoropyridines III and the 2-amino- or 2-hydrazinopyridines IV can be reacted with an alcohol or a salt thereof in the presence or advantageously in the absence of a solvent. Solvents which can be employed are those mentioned above, and furthermore ketones, eg. acetone, methyl ethyl ketone, or suitable mixtures; however, the alcohol used can also be employed directly as the solvent.

The solvent is expediently used in an amount of 100–2000% by weight, preferably 400–1200% by weight, based on the starting materials II, III or IV.

To bind the hydrogen halide eliminated during the reaction, it is expedient to add an alkali metal hydroxide or alkaline earth metal hydroxide such as lithium hydroxide, sodium hydroxide, potassium hydroxide, calcium hydroxide, magnesium hydroxide or zinc hydroxide, or an alkali metal hydrogen carbonate, alkali metal carbonate, alkaline earth metal hydrogen carbonate or alkaline earth metal carbonate of the same cations as mentioned above, or a metal alcoholate, for example a lithium alcoholate, sodium alcoholate or potassium alcoholate. The alcoholates are expediently prepared in situ by dissolving the abovementioned metals in the alcohol to be employed, or by the action of lithium hydride, sodium hydride, potassium hydride or calcium hydride. However, one of the abovementioned organic auxiliary bases can also be used.

It is advantageous to add 0.8–1.5, in particular 0.9–1.2, mol equivalents of the alcohol, expediently in the presence of an equivalent amount (of a base), or of the corresponding alcoholate to a mixture of the starting materials II, III or IV in one of the abovementioned solvents at −20°–100° C., preferably 0°–30° C., in the course of 0.25–0.5 hour and to continue stirring for 1–12 hours at 10°–120° C., preferably for 2–10 hours at 20°–80° C., until the reaction is complete, whereupon the mixture is worked up. Alternatively, the alcohol together with a base or the corresponding alcoholate can be introduced into the solvent, whereupon the starting materials II, III or IV are added under the above conditions.

The reaction can be carried out under atmospheric pressure or under elevated pressure, continuously or batchwise.

Working-up can be carried out in the same way as described for the reaction of the starting materials III, VI or VII. The compounds according to the invention are valuable precursors for the preparation of crop protection products, in particular herbicides from the class of the 1-(pyridyl) pyrazoles or of the general formula VIIIa or VIIIb below:

VIIIa or

VIIIb where the substituents have the following meanings:

Z is $OR^3$; in the case of VIIIa additionally fluorine;

$R^2$ is halogen;

$R^3$ is $C_1$–$C_6$-alkyl, $C_2$–$C_6$-alkenyl or $C_2$–$C_6$-alkynyl, it being possible for these groups to have attached to them up to 6 halogen atoms, $C_3$–$C_6$-cycloalkyl which can have attached to it up to 3 $C_1$–$C_3$-alkyl radicals, $C_1$–$C_6$-cyanoalkyl, $C_1$–$C_4$-alkoxy-$C_2$–$C_6$-alkyl, 3-oxetanyl, carboxyl-$C_1$–$C_6$-alkyl, $C_1$–$C_6$-alkoxycarbonyl-$C_1$–$C_6$-alkyl, $C_1$–$C_4$-alkoxy-$C_2$–$C_4$-alkoxycarbonyl-$C_1$–$C_6$-alkyl, aminocarbonyl-$C_1$–$C_6$-alkyl, $C_1$–$C_4$-alkylaminocarbonyl-$C_1$–$C_6$-alkyl, $C_1$–$C_4$-dialkylaminocarbonyl-$C_1$–$C_6$-alkyl, $C_2$–$C_4$-alkenylaminocarbonyl-$C_1$–$C_6$-alkyl, $C_3$–$C_4$-alkynylaminocarbonyl-$C_1$–$C_6$-alkyl, $C_1$–$C_4$-alkyl-$C_3$–$C_4$-alkenylaminocarbonyl-$C_1$–$C_6$-alkyl, $C_1$–$C_4$-alkyl-$C_3$–$C_4$-alkynylaminocarbonyl-$C_1$–$C_6$-alkyl, $C_3$–$C_6$-(α-alkylalkylidene)iminoxy-$C_2$–$C_6$-alkyl, cyclopropylmethyl, $C_1$–$C_6$-alkylamino, $C_1$–$C_6$-dialkylamino, $C_1$–$C_6$-alkylideneimino- or α-($C_1$–$C_4$-alkyl)-$C_2$–$C_6$-alkylideneimino, $R^4$ is hydrogen, $C_1$–$C_3$-alkyl, halogen, $C_1$–$C_3$-haloalkyl;

$R^5$ is $C_1$–$C_4$-alkyl, $C_2$–$C_4$-alkenyl, $C_2$–$C_4$-alkynyl, $C_1$–$C_4$-alkoxy, $C_3$–$C_4$-alkenyloxy, $C_3$–$C_4$-alkynyloxy, each of which can be substituted by 1–6 halogen atoms; $NO_2$, cyano, halogen, thiocyanato, amino, furthermore a radical $C(=O)R^7$, $S(O)_nR^8$ or $NH-C(=O)R^9$;

$R^6$ is amino, halogen, thiocyanato, cyano, nitro, hydroxyl, $C_1$–$C_3$-alkyl, $C_1$–$C_3$-haloalkyl, furthermore a radical $S(O)_n R^8$, $N(R^{10})R^{11}$, $OR^{12}$, $SR^{13}$, $N=C(R^{14})-N(R^{15})R^{16}$ or, in the case of $R^4$=hydrogen, additionally $N=C(R^{17})R^{18}$;

$R^7$ is $C_1$–$C_4$-alkyl, $C_2$–$C_4$-alkenyl, $C_2$–$C_4$-alkynyl, $C_1$–$C_4$-haloalkyl, $C_1$–$C_4$-alkoxy-$C_2$–$C_4$-alkyl, $C_3$–$C_6$-cycloalkyl, $C_1$–$C_4$-alkoxy, $C_1$–$C_4$-alkylamino or $C_1$–$C_4$-dialkylamino;

$R^8$ is $C_1$–$C_4$-alkyl, $C_1$–$C_4$-haloalkyl, $C_1$–$C_4$-alkoxy, chlorine, amino or $C_1$–$C_4$-alkylamino;

$R^9$ is $C_1$–$C_4$-alkyl, $C_1$–$C_4$-haloalkyl, $C_1$–$C_4$-alkoxy-$C_1$–$C_4$-alkyl, $C_2$–$C_4$-alkenyl, $C_2$–$C_4$-alkynyl or $C_1$–$C_4$-alkoxy;

$R^{10}$ is hydrogen, $C_1$–$C_4$-alkyl or a radical $C(=O)R^7$;

$R^{11}$ is hydrogen, $C_1$–$C_4$-alkyl, $C_3$–$C_4$-alkenyl, $C_3$–$C_4$-alkynyl, a radical $C(=O)R^7$ or $S(O)_nR^8$;

$R^{12}$ is $C_1$–$C_3$-alkoxy, $C_1$–$C_3$-haloalkoxy, $C_2$–$C_4$-alkenyloxy, $C_3$–$C_4$-alkynyloxy, $C_1$–$C_5$-alkoxycarbonyl-$C_1$–$C_4$-alkyl or $C_1$–$C_4$-alkoxy-$C_2$–$C_4$-alkoxycarbonyl-$C_1$–$C_6$-alkyl;

$R^{13}$ is $C_1$–$C_4$-alkoxycarbonyl-$C_1$–$C_4$-alkyl or $C_1$–$C_4$-alkoxy-$C_2$–$C_4$-alkoxycarbonyl-$C_1$–$C_6$-alkyl;

$R^{14}$ is hydrogen or $C_1$–$C_3$-alkyl;

$R^{15}$ is $C_1$–$C_4$-alkyl;

$R^{16}$ and $R^{17}$ independently of one another are hydrogen or $C_1$–$C_4$-alkyl;

$R^{18}$ is hydrogen, $C_1$–$C_4$-alkyl, $C_1$–$C_4$-haloalkyl, $C_1$–$C_3$-alkoxy-$C_1$–$C_3$-alkyl, $C_3$–$C_6$-cycloalkyl, $C_2$–$C_4$-alkenyl or $C_2$–$C_4$-alkynyl and halogen is fluorine, chlorine, bromine or iodine, and n is 0, 1 or 2, and the N-oxides and the agriculturally useful salts of the compounds VIIIa or VIIIb.

The 1-(pyridyl)pyrazoles of the formula VIIIa or VIIIb can be obtained in various ways, for example by the processes below:

Process A:

Reaction of a pyridyl-2-hydrazine of the formula IXa where $R^2$ and Z have the abovementioned meanings with an acrylonitrile derivative of the formula X in accordance with DBP 3520 330:

IXa     X     → VIIIa

In these formulae, $R^4$ and $R^5$ have the abovementioned meanings and A is halogen, hydroxyl, alkoxy or dialkylamino.

The process is usually carried out in an inert solvent or diluent, in particular in a halogenated hydrocarbon such as dichloromethane or 1,2-dichloromethane, an alcohol such as methanol, ethanol, n-propanol, isopropanol, n-butanol, glycol, methoxyethanol, ethoxyethanol or methoxypropanol, or an ether such as tetrahydrofuran, methyl tert-butyl ether, 1,2-dimethoxyethane or 1,2-diethoxyethane. The reaction temperature is normally from 0° to 180° C., preferably 60° to 140° C.

The reactants are generally employed in approximately stoichiometric amounts, but an excess of one of the reactants can be advantageous, for example with a view to as complete a reaction as possible of the other reactant.

Process B:

Hydrolysis and decarboxylation of a 1-(pyrid-2-yl) pyrazole-4-carboxylate of the formula VIIIc where Z and $R^2$ to $R^4$ have the abovementioned meanings, in accordance with DBP 3520 330.

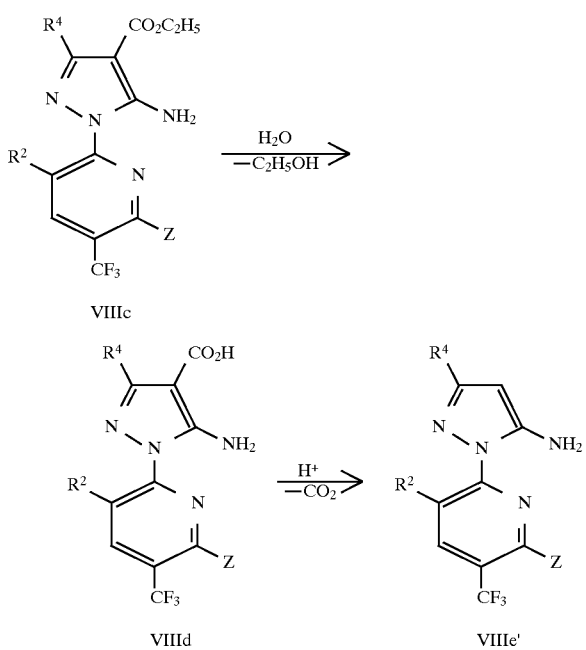

VIIIc

VIIId VIIIe'

To this end, a 1-(pyrid-2-yl)pyrazole-4-carboxylate may be hydrolyzed for 1–6 hours with dilute aqueous alkali metal hydroxide solution in the presence or absence of aqueous alcohols as solubilizers at 40°–100° C., advantageously 70°–90° C., and the carboxylic acid VIIId can then be isolated by acidifying the mixture. The pyrazole derivative VIIIe is then obtained by treating the product with dilute hydrohalic acid at 60°–120° C., advantageously 70°–90° C., expediently in the presence of a lower alcohol as solubilizer.

However, the pyrazole ester of the formula VIIIc can also be treated directly with aqueous hydrobromic acid at 60°–120° C., advantageously 70°–90° C., until hydrolysis and decarboxylation to give VIIIe' are complete.

Sodium hydroxide solution and potassium hydroxide solution are suitable as alkali metal hydroxide solutions.

Suitable alcohols are methanol, ethanol, n-propanol, iso-propanol or n-butanol.

Suitable hydrohalic acids are hydrochloric, hydrobromic and hydriodic acid.

Process C:

Reaction of a 1-(pyrid-2-yl)-5-aminopyrazole VIIIf with a reactive sulfur halogen compound XI or a reactive carbonic acid XII or a reactive amide acetal XIII

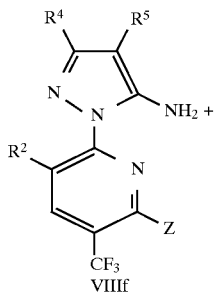

VIIIf

-continued

| Hal S(O)$_n$R$^8$ | XI | |
| or Hal—C(=O)$^7$R | XII | → VIIIa |
| or [EtO]2 C(R$^{14}$)—N(R$^{15}$)R$^{16}$ | XIII | |
| or O=C(R$^{17}$)R$^{18}$ | XIV (where R$^6$ = substituted amino) | | or a reactive keto compound XIV in accordance with DBP 3520330:

The process is usually carried out in an inert solvent or diluent, in particular a halogenated hydrocarbon such as dichloromethane or 1,2-dichloroethane, an ether such as diethyl ether, methyl tert-butyl ether, tetrahydrofuran, 1,4-dioxane or anisole, a nitrile such as acetonitrile, propionitrile or butyronitrile, an ester such as ethyl acetate, methyl propionate or ethyl propionate, or, if the presence of water does not interfere, if desired also in a two-phase mixture with water.

To bind the hydrogen halide which is liberated during the reaction with the starting materials XI–XII, it is expedient to employ bases such as, for example, alkali metal carbonates and alkali metal hydrogen carbonates such as sodium hydrogen carbonate, potassium hydrogen carbonate, sodium carbonate and potassium carbonate, alkali metal alcoholates such as sodium methanolate and potassium tert-butanolate, alkali metal hydroxides such as sodium hydroxide or potassium hydroxide. Organic bases are also advantageous: trimethylamine, triethylamine, pyridine, $\alpha$-, $\beta$-, $\gamma$-picoline, lutidine, N-dimethylaniline, N-diethylaniline, N-propylpiperidine, quinoline, isoquinoline, quinazoline, quinoxaline, triethanolamine, triamylamine, tri-n-butylamine, trifurfurylamine, trihexylamine, N-methylimidazole, N-methylpyrrole, N-ethylpiperidine, N-methylpyrrolidine, pyrazine, pyrimidine, acridine, phenanthridine, phenazine, N-dimethylcyclohexylamine or n-propyldiisopropylamine.

When reacting the reactive amide acetals XIII or the keto compound XIV, it is sufficient to stir the starting materials with or without removal of the alcohol or water of reaction which has been eliminated by means of distillation or heating on a water separator.

The reaction temperature is normally 0°–120° C., preferably 20°–80° C.

The reactants are usually employed in approximately stoichiometric amounts, but an excess of one of the reactants may also be advantageous, for example with a view to as complete a reaction as possible of the other reactant.

If an excess of the starting materials XI–XII, but at least 2 equivalents, are deliberately employed per mole of starting material VIIIf, then the result is a substitution of both amino hydrogens.

Process D:

Reaction of a 1-(pyrid-2-yl)pyrazole of the formula VIIIe' where Z, R$^2$ to R$^4$ and R$^6$ have the abovementioned meanings with electrophiles of the formula XV where B is an electron-attracting leaving group, in accordance with DE 3520 330, JO 2142–785 or EP 201 852:

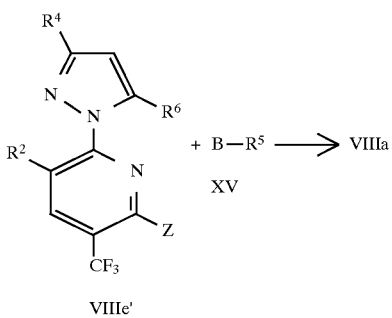

VIIIe'

The radical $R^5$ in the general formula XV is preferably chlorine, bromine, nitro, thiocyanato, formyl, alkanoyl having 1–4 carbon atoms in the alkyl moiety, $C_1$–$C_4$-alkylsulfonyl, -sulfinyl or -sulfenyl, or halomethylsulfenyl.

B is preferably halogen, in particular chlorine or bromine, or hydroxyl, alkyl- or arylsulfonyloxy, alkanoyloxy or aryloxy. Other electrophiles are sulfuryl chloride, phosphorus oxychloride/dimethylformamide, nitrating acid and other substances which can usually be used for electrophilic substitution.

The process is normally carried out in one of the abovementioned inert solvents or diluents.

The reaction temperature is normally 0°–150° C., preferably 10°–110° C.

Process E:

Diazotization of a 1-(pyrid-2-yl)-5-aminopyrazole of the formula VIIIf where Z, $R^2$, $R^4$ and $R^5$ have the abovementioned meanings and subsequent boiling to give the corresponding 5-hydroxy compound as described by Houben-Weyl, "Methoden der organischen Chemie" [Methods in Organic Chemistry], IVth Edition, Vol. 6/1C, p. 247, Georg Thieme Verlag, Stuttgart 1968, or reaction to give the corresponding fluorine compounds, ibid. Vol. 5/3, p. 213, reaction under Sandmeyer conditions to give the corresponding

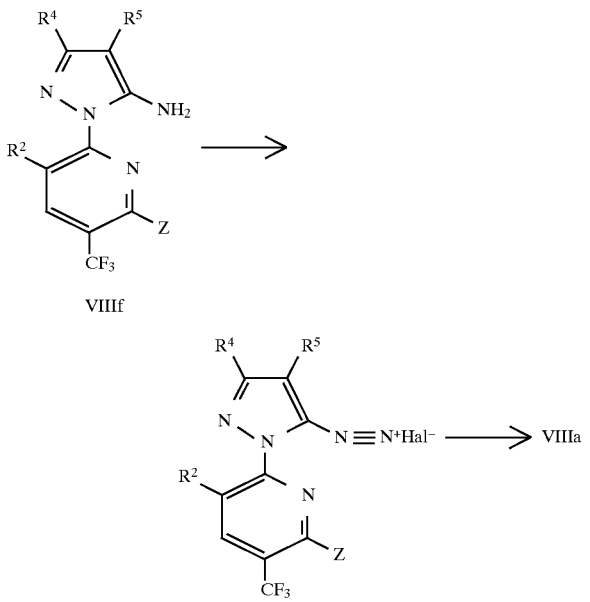

chlorine compounds, ibid. Vol. 5/3, p. 846, bromine compounds, ibid. Vol. 5/4, p. 437 or iodine compounds, ibid. Vol. 5/4, p. 639, or reaction to give the corresponding cyano compounds, ibid. Vol. 8, p. 311, or thiocyanato compounds, ibid. Vol. 9, p. 863, or reaction under Meerwein conditions to give the corresponding sulfonyl chlorides, ibid. Vol. 9, p. 579, and subsequent reaction with ammonia or amines along the lines of a Schotten-Baumann reaction, ibid. Vol. 9, p. 609, or reaction with mercaptans to give the corresponding thioethers, ibid. Vol. 9, p. 116, or with alcohols to give the corresponding ethers, ibid. Vol. 6/3, p. 81.

Process F:

Reaction of a 1-(pyrid-2-yl)-5-halopyrazole of the formula VIIIg where halogen, Z, $R^2$, $R^4$ and $R^5$ have the abovementioned meanings with amines of the formula XVI where $R^{10}$ and $R^{11}$ have the

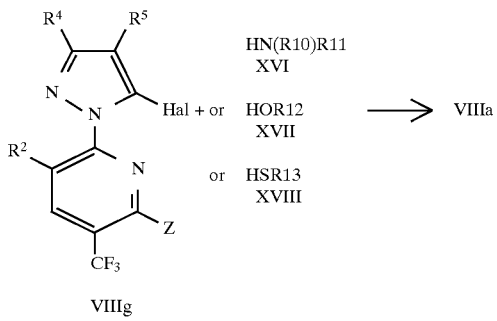

abovementioned meanings, with alcohols of the formula XVII where $R^{12}$ has the abovementioned meaning and mercaptans of the formula XVIII where $R^{13}$ has the abovementioned meaning by a similar method.

To carry out the process, 1.0–5.0 mol, preferably 1.0–2.0 mol, of the nucleophiles XVI–XVIII are generally employed per mole of 5-halopyrazole VIIIh. The reaction is carried out and the reaction products I are worked up and isolated by generally customary processes.

Suitable diluents for carrying out process F are inert organic solvents. Substances which are preferably used are aliphatic or aromatic unhalogenated or halogenated hydrocarbons such as pentane, hexane, heptane, cyclohexane, petroleum ether, toluene, xylene, methylene chloride, 1,2-dichloroethane, chlorobenzene or dichlorobenzene, ethers such as diethyl ether, diisopropyl ether, methyl tert-butyl ether, ethylene glycol dimethyl ether, tetrahydrofuran or dioxane, esters such as ethyl acetate, nitriles such as acetonitrile or propionitrile, or amides such as dimethylformamide, dimethylacetamide or N-methylpyrrolidone.

Finally, however, a suitable excess of the nucleophiles of the formula XVI–XVIII which are used as reactants can simultaneously also be used as diluents.

The process can be carried out in the absence or presence of a basic catalyst to remove the hydrogen halide which is formed. Suitable catalysts are all usual inorganic or organic bases. The bases mentioned under process C are preferably used.

However, the alkali metal salts or alkaline earth metal salts of the nucleophiles XVI–XVIII, preferably the lithium, sodium, potassium, magnesium or calcium salts, may also be used directly.

The temperatures in process F can be varied within a substantial range. In general, the process is carried out at from 0° to 150° C., preferably from 20° to 100° C.

Unless otherwise specified, all processes described above are expediently carried out under atmospheric pressure or under the inherent pressure of the reaction mixture in question.

As a rule, the reaction mixtures are worked up by methods known per se, for example by removing the solvent, partitioning the residue in a mixture of water and a suitable organic solvent, and working up the organic phase to give the product.

1-(Pyridyl)pyrazoles VIII which have CH-acidic substituents can be converted into their salts, preferably their alkali metal salts, in a manner known per se.

Salts of VIII whose metal ion is not an alkali metal ion can be prepared in the customary manner by double decomposition of the corresponding alkali metal salt, and ammonium and phosphonium salts can be prepared similarly using ammonia, phosphonium hydroxides, sulfonium hydroxides or sulfoxonium hydroxides.

Compounds VIII which have attached to them a terminal amino group can furthermore form acid addition salts. Suitable salts are generally the salts of those acids which also do not have an adverse effect on the herbicidal action of VIII, eg. the hydrochlorides and hydrobromides, sulfates, nitrates, phosphates, oxalates or the dodecylbenzenesulfonates.

Examples not according to the invention

EXAMPLE I.1

Reaction of 2-amino-3,6-dichloro-5-trifluoromethylpyridine with sodium methylate 2.6 g (0.014 mol) of 30% strength sodium methylate were added to a stirred mixture of 3.3 g (0.014 mol) of 2-amino-3,6-dichloro-5-trifluoromethylpyridine in 100 ml of methanol at 20° C. in the course of 5 minutes. First, the mixture was stirred for 1 hour at 30° C. and then for 6 hours under reflux, with HPLC monitoring, during which process the starting material was essentially the same. After cooling, the reaction mixture was concentrated in vacuo, taken up in methylene chloride and extracted using water. After drying over magnesium sulfate and concentration, the organic phase gave 3.2 g (97% of theory) of contaminated starting material.

EXAMPLE I.2

Methyl 2-amino-3-chloro-6-methoxypyridine-5-carboxylate 4.0 g (0.0173 mol) of 2-amino-3,6-dichloro-5-trifluoromethylpyridine in 20 ml of methanol were added in the course of 5 minutes at 10° C. to a stirred mixture of 5.5 g (0.0866 mol) of 88% potassium hydroxide powder in 80 ml of methanol. The reaction mixture was stirred under reflux for 10 hours with HPLC monitoring. After a further 1.1 g (0.0173 mol) of 88% potassium hydroxide powder had been added and the mixture had been refluxed for 2 hours, it was cooled and concentrated. The residue was taken up in methyl tert-butyl ether and extracted using water. After drying and concentration, 4.6 g of a resin were obtained which was stirred in pentane, filtered off with suction and then dried. Subsequent silica gel chromatography with methylene chloride gave 2.3 g (61% of theory) of the title compound of m.p. 162°–164° C. in fractions 15–50. Fractions 51–65 contained 0.3 g (6.5% of theory) of 2-amino-3,6-dichloro-S-(trimethoxymethyl)pyridine of m.p. 99°–107° C.

EXAMPLE I.3

2-Amino-3-chloro-6-methoxy-5-trifluoromethylpyridine 6.7 g (0.029 mol) of 2-amino-3,6-dichloro-5-trifluoromethylpyridine were added to a stirred mixture of 2.4 g (0.0377 mol) of 88% potassium hydroxide powder in 10 ml of methanol and 100 ml of dimethylformamide at 20° C. in the course of 5 minutes. The reaction mixture was now stirred for 89 hours at 130° C., with HPLC monitoring, a further 5 ml of methanol being added to the reaction mixture after 40 hours. After working-up in accordance with Example I.2., 0.3 g (4.6% of theory) of the title compound of $\eta_D^{24}=1.5143$ was obtained in fractions 3 and 4. Fraction 5 contained 0.7 g (10% of theory) of 2-amino-3-chloro-6-dimethylamino-5-trifluoromethylpyridine (NMR 400 MHz, CDCl$_3$ 7.58 (pyridine), 2.95 (CH$_3$)$_2$N) and fractions 9–16 contained 1.1 g (16% of theory) of starting material. Other secondary components were found in the fractions which followed.

EXAMPLE I.4

Reaction of 2,5-dichloro-6-methoxy-3-trifluoromethylpyridine with ammonia.

a) Under atmospheric pressure 6 g (0.353 mol) of gaseous ammonia were passed into a stirred mixture of 10 g (0.041 mol) of 3,6-dichloro-2-methoxy-5-trifluoromethylpyridine in 100 ml of propanol at 80°–90° C. in the course of 8 hours. According to HPLCcheck, the reaction mixture remained unchanged. Partitioning the reaction mixture in water/methyl tert-butyl ether, drying and concentrating the organic phase also showed approximately 95% pure, oily starting material according to NMR spectrum.

b) Under elevated pressure 12.4 g (0.73 mol) of gaseous ammonia were injected into a stirred mixture of 12.8 g (0.052 mol) of 3,6-dichloro-2-methoxy-5-trifluoromethylpyridine in 100 ml of methanol in an autoclave at 140° C., during which process the pressure climbed up to 200 bar. After half an hour, no starting material was detected in a sample. The reaction solution was concentrated and partitioned between methylene chloride and water. After drying, concentration, trituration of the residue with n-pentane, filtration with suction and drying, 3.4 g (28% of theory) of 2-amino-3,6-dichloro-5-trifluoromethylpyridine of m.p. 110°–112° C. were obtained. HPLC analysis revealed that the concentrated pentane filtrate (5 g) was composed of a further 19% of 2-amino-3,6-dichloro-5-trifluoromethylpyridine and 5 other compounds.

Examples according to the invention

Synthesis of the precursors

EXAMPLE II.1

2,5-Dichloro-6-methoxy-3-trifluoromethylpyridine 10.8 g (0.06 mol) of 30% strength sodium methylate solution were added with stirring at 0°–5° C. in the course of 20 minutes to 15 g (0.06 mol) of 2,3,6-trichloro-5-trifluoromethylpyridine in 200 ml of methyl tert-butyl ether, and stirring was continued for 30 minutes at the same temperature. After the mixture had been heated to 20° C., the fine precipitate which had formed was filtered off with suction and washed using methyl tert-butyl ether. The organic filtrate was washed with water, dried and concentrated, giving 14.3 g (97% of theory) of the title compound of $\eta_D^{25}=1.4890$ (Table III, No. 3.001).

EXAMPLE II.2

2,5-Dichloro-6-propargyloxy-3-trifluoromethylpyridine 9.5 g (0.3952 mol) of sodium hydride were introduced into 500 ml of diethyl ether while flushing with nitrogen. 50 ml of propargyl alcohol were passed in, with stirring, in the course of 30 minutes and stirring was continued at 20° C. for a further 30 minutes. 90 g (0.3593 mol) of 2,3,6-trichloro-5-trifluoromethylpyridine in 150 ml of diethyl ether were added at 0°–5° C. with stirring in the course of 20 minutes, during which process a fine precipitate was formed. After the mixture had been heated to 20° C., the procedure was as described in Example II.1, giving 96 g (99% of theory) of the title compound of $\eta^{24}{}_D$=1.5038 (Table III, No. 3.035).

EXAMPLE II.3

3-Chloro-2,6-difluoro-5-trifluoromethylpyridine 110.3 g (0.44 mol) of 2,3,6-trichloro-5-trifluoromethylpyridine and 58.7 g (1.01 mol) of potassium fluoride were added, with stirring, to 500 ml of sulfolane (dried using thionyl chloride as described on p. 13) and the mixture was stirred for 2½ hours at 150°–160° C. with HPLC monitoring. After cooling to 50° C., 93 g (98% of theory) of the title compound were distilled off from the reaction mixture at 40°–45° C., 25 mbar. NMR (400 MHz, CDCl$_3$) δ 8.2 pyrH/t; $\eta_D{}^{23}$=1.4229.

EXAMPLE II.4

2-Amino-3-chloro-6-fluoro-5-trifluoromethylpyridine 12.5 g (0.74 mol) of gaseous ammonia were passed into a stirred mixture of 40 g (0.184 mol) of 3-chloro-2,6-difluoro-5-trifluoromethylpyridine in 200 ml of ethanol in the course of 45 minutes at 50°–60° C. After the reaction mixture had been stirred for 1½ hours at 55° C., it was cooled and concentrated. The residue was stirred in water, filtered off with suction and dried, giving 36.7 g (93% of theory) of the title compound of m.p. 101°–103° C.

EXAMPLE II.5

3-Chloro-6-fluoro-2-hydrazino-5-trifluoromethylpyridine 10.5 g (0.21 mol) of hydrazine hydrate were added to a stirred mixture of 21.8 g (0.1 mol) of 3-chloro-2,6-difluoro-5-trifluoromethylpyridine in 100 ml of propanol at 50° C. in the course of 15 minutes, and stirring was continued for 2 hours at the same temperature. After cooling, the batch was poured into 1.5 l of water and the precipitate which had separated out was filtered off with suction. It was taken up in ethyl acetate for purification and extracted using water. After drying and concentration, 20.9 g (91% of theory) of the title compound of m.p. 104°–106° C. were obtained; a sublimated sample melted at 111°–113° C.

Synthesis of the end products

EXAMPLE III.1

3-Chloro-6-fluoro-2-propargyloxy-5-trifluoromethylpyridine 47.3 g (0.175 mol) of 2,5-dichloro-6-propargyloxy-3-trifluoromethylpyridine, 0.5 g (1.89 mmol) of 18-crown-6 and 15.2 g (0.263 mol) of potassium fluoride were added to 150 ml of sulfolane and the mixture was stirred for 5 hours at 150°–155° C. After cooling, the reaction mixture was stirred with methyl tert-butyl ether and separated from the inorganic precipitate. The filtrate was extracted four times using water, dried and concentrated. The residue together with methylene chloride was filtered with suction through a silica gel frit and concentrated, giving 31.4 g (71% of theory) of the title compound of $\eta_D{}^{24}$=1.4732 (Table III, No. 3.036).

EXAMPLE III.2

2-Amino-3-chloro-6-methoxy-5-trifluoromethylpyridine 4.6 g (0.0256 mol) of a 30% strength sodium methylate solution were added to a stirred mixture of 5.5 g (0.0256 mol) of 2-amino-3-chloro-6-fluoro-4-trifluoromethylpyridine in 80 ml of methanol at 22°–27° C. in the course of 5 minutes. After the reaction mixture had been stirred for 6 hours under reflux it was cooled, concentrated and partitioned in methylene chloride/water. The organic phase was separated off, dried and chromatographed over a silica gel column, giving 5.0 g (86% of theory) of the title compound of $\eta_D{}^{24}$=1.5143. NMR (400 MHz, CDCl$_3$) δ 7.6, pyr (1/s); 3.91, CH$_3$O (3/s) (Table I, No. 1.001).

EXAMPLE III.3

2-Amino-3-chloro-6-propargyloxy-5-trifluoromethylpyridine 3.9 g (0.153 mol) of sodium hydride were introduced, under nitrogen, into 250 ml of methyl tert-butyl ether, with stirring, and 20 ml of propargyl alcohol were then added dropwise with stirring at 25°–30° C. over 20 minutes. After the mixture had been stirred for 30 minutes at 25° C., 32.9 g (0.153 mol) of 2-amino-3-chloro-6-fluoro-5-trifluoromethylpyridine in 100 ml of methyl tert-butyl ether were added in the course of 10 minutes and the mixture was stirred for 14 hours at 25° C. The reaction mixture was extracted with water, dried and concentrated, giving 37.8 g (99% of theory) of the title compound as a colorless oil of $\eta_D{}^{24}$=1.5217 (Table I, No. 1.035).

EXAMPLE III.4

2-Amino-5-chloro-6-methoxy-3-trifluoromethylpyridine 16.2 g (0.954 mol) of gaseous ammonia were injected into an autoclave containing 36.5 g (0.159 mol) of 3-chloro-6-fluoro-2-methoxy-5-trifluoromethylpyridine and 150 ml of ethanol and the mixture was then stirred for 15 hours at 110° C. After cooling and releasing the pressure, the reaction mixture was concentrated and the residue was partitioned in methylene chloride/water. After 0.4 g of insoluble matter had been separated off, the organic phase was separated off, and the aqueous phase was reextracted twice using methylene chloride. The organic extracts were dried and concentrated, giving 30.6 g (85% of theory) of the title compound as an oil. NMR (400 MHz, CDCl$_3$) δ 7.6 pyr (1/s); 3.95 CH$_3$O (3/s); 4.9 NH$_2$(2/s). After silica gel chromatography with methylene chloride, a further 33.2 g (72% of theory) of the title compound were obtained as a colorless oil of $\eta_D{}^{24}$=1.5140 (Table II, No. 2.001).

EXAMPLE III.5

2-Amino-5-chloro-6-propargyloxy-3-trifluoromethylpyridine

Starting from 3.1 g (0.182 mol) of ammonia and 10 g (0.039 mol) of 3-chloro-6-fluoro-2-propargyloxy-5-trifluoromethylpyridine, 4.1 g (42.3% of theory) of the title compound of m.p. 56°–58° C. (Table II, No. 2.035) and 2.7 g (27% of theory) of reisolated starting material were obtained after stirring for 3 hours at 110° C. under the same conditions as described in Example III.4.

EXAMPLE III.6

3-Chloro-6-hydrazino-2-methoxy-5-trifluoromethylpyridine 10.7 g (0.214 mol) of hydrazine hydrate were added at 50° C. in the course of 10 minutes with stirring to 25.0 g (0.102 mol) of 2,5-dichloro-6-methoxy-3-trifluoromethylpyridine in 100 ml of propanol and the mixture was stirred for 3 hours at 90° C. After cooling, the resulting suspension was poured into 1.2 liters of water, and the precipitate was filtered off with suction, taken up in methylene chloride and washed with water. The organic phase was dried and concentrated, and the residue was stirred with ether/pentane (1:1). After filtration with suction and drying, 7.8 g (32% of theory) of the title compound of m.p. 140°–142° C. (Table II, No. 2.011) were obtained.

EXAMPLE III.7.

3-Chloro-6-hydrazino-2-propargyloxy-5-trifluoromethylpyridine

Starting from 7.8 g (0.155 mol) of hydrazine hydrate and 20 g (0.074 mol) of 2, 5-dichloro-6-propargyloxy-3-trifluoromethylpyridine, 11.0 g (56% of theory) of the title compound were obtained as a colorless powder of m.p. 98°–102° C. (Table II, No. 2.036) under the conditions of Example III.4.

Other compounds Ia and Ib which have been prepared, or can be prepared, by one of the processes described are listed in the tables which follow.

TABLE 1

$$\text{CF}_3 \diagdown \text{pyridine ring with } R^2, R^1, R^3O, N \text{ substituents} \quad \text{Ia}$$

| No. | $R^1$ | $R^2$ | $R^3$ | m.p. (0° C.), $\eta_D^{25}$, $^1$H NMR (ppm), |
|---|---|---|---|---|
| 1.001 | $NH_2$ | Cl | $CH_3$ | $\eta_D^{24} = 1.5143$ |
| 1.002 | $NH_2$ | Cl | $C_2H_5$ | $\eta_D^{23} = 1.5040$ |
| 1.003 | $NH_2$ | Cl | $n\text{-}C_3H_7$ | |
| 1.004 | $NH_2$ | Cl | $i\text{-}C_3H_7$ | |
| 1.005 | $NH_2$ | Cl | $n\text{-}C_4H_9$ | |
| 1.006 | $NH_2$ | Cl | $i\text{-}C_4H_9$ | |
| 1.007 | $NH_2$ | Cl | $sec\text{-}C_4H_9$ | |
| 1.008 | $NH_2$ | Cl | $CH_2\text{-}CH(CH_3)_2$ | |
| 1.009 | $NH_2$ | Cl | $n\text{-}C_5H_{11}$ | |
| 1.010 | $NH_2$ | Cl | $n\text{-}C_6H_{13}$ | |
| 1.011 | $NHNH_2$ | Cl | $CH_3$ | |
| 1.012 | $NHNH_2$ | Cl | $C_2H_5$ | |
| 1.013 | $NHNH_2$ | Cl | $n\text{-}C_3H_7$ | |
| 1.014 | $NHNH_2$ | Cl | $i\text{-}C_3H_7$ | |
| 1.015 | $NHNH_2$ | Cl | $n\text{-}C_4H_9$ | |
| 1.016 | $NHNH_2$ | Cl | $i\text{-}C_4H_9$ | |
| 1.017 | $NHNH_2$ | Cl | $sec.\text{-}C_4H_9$ | |
| 1.018 | $NHNH_2$ | Cl | $CH_2\text{-}CH(CH_3)_2$ | |
| 1.019 | $NHNH_2$ | Cl | $n\text{-}C_5H_{11}$ | |
| 1.020 | $NHNH_2$ | Cl | $n\text{-}C_6H_{13}$ | |
| 1.021 | $NH_2$ | Cl | $CH=CH_2$ | |
| 1.022 | $NH_2$ | Cl | $C(CH_3)=CH_2$ | |
| 1.023 | $NH_2$ | Cl | $CH_2\text{-}CH=CH_2$ | |
| 1.024 | $NH_2$ | Cl | $CH_2\text{-}C(CH_3)=CH_2$ | |
| 1.025 | $NH_2$ | Cl | $CH_2\text{-}CH=CH\text{-}CH_3$ | |
| 1.026 | $NH_2$ | Cl | $CH_2\text{-}CH=CHCl$ | |
| 1.027 | $NH_2$ | Cl | $CH_2\text{-}C(Cl)=CH_2$ | |
| 1.028 | $NHNH_2$ | Cl | $CH=CH_2$ | |
| 1.029 | $NHNH_2$ | Cl | $C(CH_3)=CH_2$ | |
| 1.030 | $NHNH_2$ | Cl | $CH_2\text{-}CH=CH_2$ | |
| 1.031 | $NHNH_2$ | Cl | $CH_2\text{-}C(CH_3)=CH_2$ | |
| 1.032 | $NHNH_2$ | Cl | $CH_2\text{-}CH=CH\text{-}CH_3$ | |
| 1.033 | $NHNH_2$ | Cl | $CH_2\text{-}CH=CHCl$ | |
| 1.034 | $NHNH_2$ | Cl | $CH_2\text{-}C(Cl)=CH_2$ | |
| 1.035 | $NH_2$ | Cl | $CH_2\text{-}C\equiv CH$ | $\eta_D^{24} = 1.5217$ |
| 1.036 | $NHNH_2$ | Cl | $CH_2\text{-}4\,C\equiv CH$ | |
| 1.037 | $NH_2$ | Cl | $CH(CH_3)\text{-}C\equiv CH$ | |
| 1.038 | $NH_2$ | Cl | $CH_2\text{-}C\equiv C\text{-}CH_3$ | |
| 1.039 | $NH_2$ | Cl | $CH_2\text{-}C\equiv C\text{-}CH_2Cl$ | |
| 1.040 | $NH_2$ | Cl | cyclopropyl | |
| 1.041 | $NH_2$ | Cl | cyclobutyl | |
| 1.042 | $NH_2$ | Cl | cyclopentyl | |
| 1.043 | $NH_2$ | Cl | cyclohexyl | |
| 1.044 | $NHNH_2$ | Cl | cyclopropyl | |
| 1.045 | $NHNH_2$ | Cl | cyclobutyl | |
| 1.046 | $NHNH_2$ | Cl | cyclopentyl | |
| 1.047 | $NHNH_2$ | Cl | cyclohexyl | |
| 1.048 | $NH_2$ | Cl | $CH_2CN$ | |
| 1.049 | $NH_2$ | Cl | $CH_2\text{-}CH_2CN$ | |
| 1.050 | $NH_2$ | Cl | $CH_2\text{-}CH_2\text{-}CH_2CN$ | |
| 1.051 | $NH_2$ | Cl | $CH(CH_3)\text{-}CH_2CN$ | |
| 1.052 | $NHNH_2$ | Cl | $CH_2CN$ | |

TABLE 1-continued

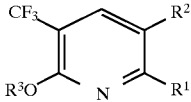

| No. | R¹ | R² | R³ | m.p. (0° C.), $n_D^{25}$, $^1$H NMR (ppm), |
|---|---|---|---|---|
| 1.053 | NHNH$_2$ | Cl | CH$_2$—CH$_2$CN | |
| 1.054 | NHNH$_2$ | Cl | CH$_2$—CH$_2$—CH$_2$CN | |
| 1.055 | NHNH$_2$ | Cl | CH(CH$_3$)—CH$_2$CN | |
| 1.056 | NH$_2$ | Cl | CH$_2$—CH$_2$—OCH$_3$ | |
| 1.057 | NH$_2$ | Cl | CH$_2$—CH$_2$—OC$_2$H$_5$ | |
| 1.058 | NH$_2$ | Cl | CH$_2$—CH$_2$—O-n-C$_3$H$_7$ | |
| 1.059 | NH$_2$ | Cl | CH$_2$—CH$_2$—CH$_2$—OCH$_3$ | |
| 1.060 | NHNH$_2$ | Cl | CH$_2$—CH$_2$—OCH$_3$ | |
| 1.061 | NHNH$_2$ | Cl | CH$_2$—CH$_2$—OC$_2$H$_5$ | |
| 1.062 | NHNH$_2$ | Cl | CH$_2$—CH$_2$—O-n-C$_3$H$_7$ | |
| 1.063 | NHNH$_2$ | Cl | CH$_2$—CH$_2$—CH$_2$—OCH$_3$ | |
| 1.064 | NH$_2$ | Cl | 3-oxetanyl | |
| 1.065 | NHNH$_2$ | Cl | 3-oxetanyl | |
| 1.066 | NH$_2$ | Cl | CH$_2$—CH$_2$—CO$_2$H | |
| 1.067 | NH$_2$ | Cl | CH(CH$_3$)—CO$_2$H | |
| 1.068 | NH$_2$ | Cl | CH$_2$—CH$_2$—CH$_2$—CO$_2$H | |
| 1.069 | NHNH$_2$ | Cl | CH$_2$—CH$_2$—CO$_2$H | |
| 1.070 | NHNH$_2$ | Cl | CH(CH3)—CO2H | |
| 1.071 | NHNH$_2$ | Cl | CH$_2$—CH$_2$—CH$_2$—CO$_2$H | |
| 1.072 | NH$_2$ | Cl | CH$_2$—CO$_2$CH$_3$ | 103–107 |
| 1.073 | NH$_2$ | Cl | CH$_2$—CO$_2$C$_2$H$_5$ | |
| 1.074 | NH$_2$ | Cl | CH$_2$—CO$_2$-n-C$_3$H$_7$ | |
| 1.075 | NH$_2$ | Cl | CH$_2$CO$_2$-n-C$_4$H$_9$ | |
| 1.076 | NH$_2$ | Cl | CH$_2$CO$_2$-n-C$_5$H$_{11}$ | |
| 1.077 | NH$_2$ | Cl | CH(CH$_3$)—CO$_2$CH$_3$ | |
| 1.078 | NH$_2$ | Cl | CH(CH$_3$)—CO$_2$C$_2$H$_5$ | |
| 1.079 | NH$_2$ | Cl | CH(CH$_3$)—CO$_2$-n-C$_3$H$_7$ | |
| 1.080 | NHNH$_2$ | Cl | CH$_2$—CO$_2$CH$_3$ | |
| 1.081 | NHNH$_2$ | Cl | CH$_2$—CO$_2$C$_2$H$_5$ | |
| 1.082 | NHNH$_2$ | Cl | CH$_2$—CO$_2$-n-C$_3$H$_7$ | |
| 1.083 | NHNH$_2$ | Cl | CH$_2$—CO$_2$-n-C$_4$H$_9$ | |
| 1.084 | NHNH$_2$ | Cl | CH$_2$—CO$_2$-n-C$_5$H$_{11}$ | |
| 1.085 | NHNH$_2$ | Cl | CH(CH$_3$)—CO$_2$CH$_3$ | |
| 1.086 | NHNH$_2$ | Cl | CH(CH$_3$)—CO$_2$C$_2$H$_5$ | |
| 1.087 | NHNH$_2$ | Cl | CH(CH$_3$)—CO$_2$-n-C$_3$H$_7$ | |
| 1.088 | NH$_2$ | Cl | CH$_2$—CO$_2$—CH$_2$—CH$_2$—OCH$_3$ | |
| 1.089 | NH$_2$ | Cl | CH$_2$—CO$_2$—CH$_2$—CH$_2$—OC$_2$H$_5$ | |
| 1.090 | NH$_2$ | Cl | CH(CH$_3$)—CO$_2$—CH$_2$—CH$_2$—OCH$_3$ | |
| 1.091 | NH$_2$ | Cl | CH(CH$_3$)—CO$_2$—CH$_2$—CH$_2$—OC$_2$H$_5$ | |
| 1.092 | NHNH$_2$ | Cl | CH$_2$—CO$_2$—CH$_2$—CH$_2$—OCH$_3$ | |
| 1.093 | NHNH$_2$ | Cl | CH$_2$—CO$_2$—CH$_2$—CH$_2$—OC$_2$H$_5$ | |
| 1.094 | NHNH$_2$ | Cl | CH(CH$_3$)—CO$_2$—CH$_2$—CH$_2$—OCH$_3$ | |
| 1.095 | NHNH$_2$ | Cl | CH(CH$_3$)—CO$_2$—CH$_2$—CH$_2$—OC$_2$H$_5$ | |
| 1.096 | NH$_2$ | Cl | CH$_2$—CO—NH—CH$_3$ | |
| 1.097 | NH$_2$ | Cl | CH$_2$—CO—NH—C$_2$H$_5$ | |
| 1.098 | NH$_2$ | Cl | CH$_2$—CO—NH-n-C$_3$H$_7$ | |
| 1.099 | NH$_2$ | Cl | CH$_2$—CO—NH-i-C$_3$H$_7$ | |
| 1.100 | NH$_2$ | Cl | CH$_2$—CO—NH-n-C$_4$H$_9$ | |
| 1.101 | NHNH$_2$ | Cl | CH$_2$—CO—NH—CH$_3$ | |
| 1.102 | NHNH$_2$ | Cl | CH$_2$—CO—NH—C$_2$H$_5$ | |
| 1.103 | NHNH$_2$ | Cl | CH$_2$—CO—NH-n-C$_3$H$_7$ | |
| 1.104 | NHNH$_2$ | Cl | CH$_2$—CO—NH-i-C$_3$H$_7$ | |
| 1.105 | NHNH$_2$ | Cl | CH$_2$—CO—NH-n-C$_4$H$_9$ | |
| 1.106 | NH$_2$ | Cl | CH(CH$_3$)—CO—NH—CH$_3$ | |
| 1.107 | NH$_2$ | Cl | CH(CH$_3$)—CO—NH—C$_2$H$_5$ | |
| 1.108 | NH$_2$ | Cl | CH(CH$_3$)—CO—NH-n-C$_3$H$_7$ | |
| 1.109 | NH$_2$ | Cl | CH(CH$_3$)—CO—NH-i-C$_3$H$_7$ | |
| 1.110 | NH$_2$ | Cl | CH(CH$_3$)—CO—NH-n-C$_4$H$_9$ | |
| 1.111 | NHNH$_2$ | Cl | CH(CH$_3$)—CO—NH—CH$_3$ | |
| 1.112 | NHNH$_2$ | Cl | CH(CH$_3$)—CO—NH—C$_2$H$_5$ | |
| 1.113 | NHNH$_2$ | Cl | CH(CH$_3$)—CO—NH-n-C$_3$H$_7$ | |
| 1.114 | NHNH$_2$ | Cl | CH(CH$_3$)—CO—NH-i-C$_3$H$_7$ | |
| 1.115 | NHNH$_2$ | Cl | CH(CH$_3$)—CO—NH-n-C$_4$H$_9$ | |
| 1.116 | NH$_2$ | Cl | CH$_2$—CO—N(CH$_3$)$_2$ | |
| 1.117 | NH$_2$ | Cl | CH$_2$—CO—N(CH$_3$)—C$_2$H$_5$ | |
| 1.118 | NH$_2$ | Cl | CH$_2$—CO—N(C$_2$H$_5$)$_2$ | |
| 1.119 | NH$_2$ | Cl | CH$_2$—CO—N(n-C$_3$H$_7$)$_2$ | |
| 1.120 | NHNH$_2$ | Cl | CH$_2$—CO—N(CH$_3$)2 | |
| 1.121 | NHNH$_2$ | Cl | CH$_2$—CO—N(CH$_3$)—C$_2$H$_5$ | |
| 1.122 | NHNH$_2$ | Cl | CH$_2$—CO—N(C$_2$H$_5$)$_2$ | |

TABLE 1-continued

Structure Ia: pyridine with CF$_3$ at position 3, R$^2$ at position 5, R$^3$O at position 6, R$^1$ at position 2.

| No. | R$^1$ | R$^2$ | R$^3$ | m.p. (0° C.), η$_D^{25}$, $^1$H NMR (ppm) |
|---|---|---|---|---|
| 1.123 | NHNH$_2$ | Cl | CH$_2$—CO—N(n-C$_3$H$_7$)$_2$ | |
| 1.124 | NH$_2$ | Cl | CH(CH$_3$)—CO—N(CH$_3$)$_2$ | |
| 1.125 | NH$_2$ | Cl | CH(CH$_3$)—CO—N(CH$_3$)—C$_2$H$_5$ | |
| 1.126 | NH$_2$ | Cl | CH(CH$_3$)—CO—N(C$_2$H$_5$)$_2$ | |
| 1.127 | NH$_2$ | Cl | CH(CH$_3$)—CO—N(n-C$_3$H$_7$)$_2$ | |
| 1.128 | NHNH$_2$ | Cl | CH(CH$_3$)—CO—N(CH$_3$)$_2$ | |
| 1.129 | NHNH$_2$ | Cl | CH(CH$_3$)—CO—N(CH$_3$)—C$_2$H$_5$ | |
| 1.130 | NHNH$_2$ | Cl | CH(CH$_3$)—CO—N(C$_2$H$_5$)$_2$ | |
| 1.131 | NHNH$_2$ | Cl | CH(CH$_3$)—CO—N(n-C$_3$H$_7$)$_2$ | |
| 1.132 | NH$_2$ | Cl | CH$_2$—CO—NH—CH=CH$_2$ | |
| 1.133 | NH$_2$ | Cl | CH$_2$—CO—NH—CH$_2$—CH=CH$_2$ | |
| 1.134 | NHNH$_2$ | Cl | CH$_2$—CO—NH—CH=CH$_2$ | |
| 1.135 | NHNH$_2$ | Cl | CH$_2$—CO—NH—CH$_2$—CH=CH$_2$ | |
| 1.136 | NH$_2$ | Cl | CH(CH$_3$)—CO—NH—CH=CH$_2$ | |
| 1.137 | NH$_2$ | Cl | CH(CH$_3$)—CO—NH—CH$_2$—CH=CH$_2$ | |
| 1.138 | NHNH$_2$ | Cl | CH(CH$_3$)—CO—NH—CH=CH$_2$ | |
| 1.139 | NHNH$_2$ | Cl | CH(CH$_3$)—CO—NH—CH$_2$—CH=CH$_2$ | |
| 1.140 | NH$_2$ | Cl | CH$_2$—CO—NH—CH$_2$—C≡CH | |
| 1.141 | NH$_2$ | Cl | CH(CH$_3$)—CO—NH—CH$_2$—C≡CH | |
| 1.142 | NHNH$_2$ | Cl | CH$_2$—CO—NH—CH$_2$—C≡CH | |
| 1.143 | NHNH$_2$ | Cl | CH(CH$_3$)—CO—NH—CH$_2$—C≡CH | |
| 1.144 | NH$_2$ | Cl | CH$_2$—CO—N(CH$_3$)CH$_2$—CH=CH$_2$ | |
| 1.145 | NH$_2$ | Cl | CH(CH$_3$)—CO—N(CH$_3$)—CH$_2$—CH=CH$_2$ | |
| 1.146 | NHNH$_2$ | Cl | CH$_2$—CO—N(CH$_3$)CH$_2$—CH=CH$_2$ | |
| 1.147 | NHNH$_2$ | Cl | CH(CH$_3$)—CO—N(CH$_3$)—CH$_2$—CH=CH$_2$ | |
| 1.148 | NH$_2$ | Cl | CH$_2$—CO—N(CH$_3$)—CH$_2$—C≡CH | |
| 1.149 | NH$_2$ | Cl | CH(CH$_3$)—CO—N(CH$_3$)—CH$_2$—C≡CH | |
| 1.150 | NHNH$_2$ | Cl | CH$_2$—CO—N(CH$_3$)—CH$_2$—C≡CH | |
| 1.151 | NHNH$_2$ | Cl | CH(CH$_3$)—CO—N(CH$_3$)—CH$_2$—C≡CH | |
| 1.152 | NH$_2$ | Cl | CH$_2$—CH$_2$—O—N=C(CH$_3$)—CH$_3$ | |
| 1.153 | NHNH$_2$ | Cl | CH$_2$—CH$_2$—O—N=C(CH$_3$)—CH$_3$ | |
| 1.154 | NH$_2$ | Cl | CH$_2$-cyclopropyl | |
| 1.155 | NHNH$_2$ | Cl | CH$_2$-cyclopropyl | |
| 1.156 | NH$_2$ | Cl | NH—CH$_3$ | |
| 1.157 | NH$_2$ | Cl | NH—C$_2$H$_5$ | |
| 1.158 | NH$_2$ | Cl | NH-n-C$_3$H$_7$ | |
| 1.159 | NHNH$_2$ | Cl | NH—CH$_3$ | |
| 1.160 | NHNH$_2$ | Cl | NH—C$_2$H$_5$ | |
| 1.161 | NHNH$_2$ | Cl | NH-n-C$_3$H$_7$ | |
| 1.162 | NH$_2$ | Cl | N(CH$_3$)$_2$ | |
| 1.163 | NH$_2$ | Cl | N(CH$_3$)—C$_2$H$_5$ | |
| 1.164 | NH$_2$ | Cl | N(C$_2$H$_5$)$_2$ | |
| 1.165 | NHNH$_2$ | Cl | N(CH$_3$)$_2$ | |
| 1.166 | NHNH$_2$ | Cl | N(CH$_3$)—C$_2$H$_5$ | |
| 1.167 | NHNH$_2$ | Cl | N(C$_2$H$_5$)$_2$ | |
| 1.168 | NH$_2$ | Cl | N=CH—CH$_3$ | |
| 1.169 | NH$_2$ | Cl | N=CH—C$_2$H$_5$ | |
| 1.170 | NH$_2$ | Cl | N=CH-n-C$_3$H$_7$ | |
| 1.171 | NHNH$_2$ | Cl | N=CH—CH$_3$ | |
| 1.172 | NHNH$_2$ | Cl | N=CH—C$_2$H$_5$ | |
| 1.173 | NHNH$_2$ | Cl | N=CH-n-C$_3$H$_7$ | |
| 1.174 | NH$_2$ | Cl | N=C(CH$_3$)—CH$_3$ | |
| 1.175 | NH$_2$ | Cl | N=C(CH$_3$)—C$_2$H$_5$ | |
| 1.176 | NHNH$_2$ | Cl | N=C(CH$_3$)—CH$_3$ | |
| 1.177 | NHNH$_2$ | Cl | N=C(CH$_3$)—C$_2$H$_5$ | |
| 1.178 | NHNH$_2$ | Cl | C(CH)$_3$—C≡CH | |
| 1.179 | NHNH$_2$ | Cl | CH$_2$—C≡C—CH$_3$ | |
| 1.180 | NHNH$_2$ | Cl | CH$_2$—C≡C—CH$_2$Cl | |
| 1.181 | NH$_2$ | Cl | CH$_2$CO$_2$H | |
| 1.182 | NHNH$_2$ | Cl | CH$_2$CO$_2$H | |

TABLE 2

Ib

[Structure: pyridine with R² at position, CF₃, R³O, N, R¹]

| No. | R¹ | R² | R³ | m.p. (0° C.), $\eta_D^{25}$, ¹H NMR (ppm), |
|---|---|---|---|---|
| 2.001 | NH₂ | Cl | CH₃ | $\eta_D^{24}$ = 1.5140 |
| 2.002 | NH₂ | Cl | C₂H₅ | |
| 2.003 | NH₂ | Cl | n-C₃H₇ | |
| 2.004 | NH₂ | Cl | i-C₃H₇ | $\eta_D^{24}$ = 1.4938 |
| 2.005 | NH₂ | Cl | n-C₄H₉ | |
| 2.006 | NH₂ | Cl | i-C₄H₉ | |
| 2.007 | NH₂ | Cl | sec-C₄H₉ | |
| 2.008 | NH₂ | Cl | CH₂—CH(CH₃)₂ | |
| 2.009 | NH₂ | Cl | n-C₅H₁₁ | |
| 2.010 | NH₂ | Cl | n-C₆H₁₃ | |
| 2.011 | NHNH₂ | Cl | CH₃ | 140–142 |
| 2.012 | NHNH₂ | Cl | C₂H₅ | 116–118 |
| 2.013 | NHNH₂ | Cl | n-C₃H₇ | |
| 2.014 | NHNH₂ | Cl | i-C₃H₇ | |
| 2.015 | NHNH₂ | Cl | n-C₄H₉ | |
| 2.016 | NHNH₂ | Cl | i-C₄H₉ | |
| 2.017 | NHNH₂ | Cl | sec.-C₄H₉ | |
| 2.018 | NHNH₂ | Cl | CH₂—CH(CH₃)₂ | |
| 2.019 | NHNH₂ | Cl | n-C₅H₁₁ | |
| 2.020 | NHNH₂ | Cl | n-C₆H₁₃ | |
| 2.021 | NH₂ | Cl | CH═CH₂ | |
| 2.022 | NH₂ | Cl | C(CH₃)═CH₂ | |
| 2.023 | NH₂ | Cl | CH₂—CH═CH₂ | |
| 2.024 | NH₂ | Cl | CH₂—C(CH₃)═CH₂ | |
| 2.025 | NH₂ | Cl | CH₂—CH═CH—CH₃ | |
| 2.026 | NH₂ | Cl | CH₂—CH═CHCl | |
| 2.027 | NH₂ | Cl | CH₂—C(Cl)═CH₂ | |
| 2.028 | NHNH₂ | Cl | CH═CH₂ | |
| 2.029 | NHNH₂ | Cl | C(CH₃)═CH₂ | |
| 2.030 | NHNH₂ | Cl | CH₂—CH═CH₂ | |
| 2.031 | NHNH₂ | Cl | CH₂—C(CH₃)═CH₂ | |
| 2.032 | NHNH₂ | Cl | CH₂—CH═CH—CH₃ | |
| 2.033 | NHNH₂ | Cl | CH₂—CH═CHCl | |
| 2.034 | NHNH₂ | Cl | CH₂—C(Cl)═CH₂ | |
| 2.035 | NH₂ | Cl | CH₂—C≡CH | 56–58 |
| 2.036 | NHNH₂ | Cl | CH₂—C≡CH | 98–102 |
| 2.037 | NH₂ | Cl | CH(CH₃)—C≡CH | |
| 2.038 | NH₂ | Cl | CH₂—C≡C—CH₃ | |
| 2.039 | NH₂ | Cl | CH₂—C≡C—CH₂Cl | |
| 2.040 | NH₂ | Cl | cyclopropyl | |
| 2.041 | NH₂ | Cl | cyclobutyl | |
| 2.042 | NH₂ | Cl | cyclopentyl | |
| 2.043 | NH₂ | Cl | cyclohexyl | |
| 2.044 | NHNH₂ | Cl | cyclopropyl | |
| 2.045 | NHNH₂ | Cl | cyclobutyl | |
| 2.046 | NHNH₂ | Cl | cyclopentyl | |
| 2.047 | NHNH₂ | Cl | cyclohexyl | |
| 2.048 | NH₂ | Cl | CH₂CN | |
| 2.049 | NH₂ | Cl | CH₂—CH₂CN | |
| 2.050 | NH₂ | Cl | CH₂—CH₂—CH₂CN | |
| 2.051 | NH₂ | Cl | CH(CH₃)—CH₂CN | |
| 2.052 | NHNH₂ | Cl | CH₂CN | |
| 2.053 | NHNH₂ | Cl | CH₂—CH₂CN | 138–140 |
| 2.054 | NHNH₂ | Cl | CH₂—CH₂—CH₂CN | |
| 2.055 | NHNH₂ | Cl | CH(CH₃)—CH₂CN | |
| 2.056 | NH₂ | Cl | CH₂—CH₂—OCH₃ | 89–91 |
| 2.057 | NH₂ | Cl | CH₂—CH₂—OC₂H₅ | |
| 2.058 | NH₂ | Cl | CH₂—CH₂—O-n-C₃H₇ | |
| 2.059 | NH₂ | Cl | CH₂—CH₂—CH₂—OCH₃ | |
| 2.060 | NHNH₂ | Cl | CH₂—CH₂—OCH₃ | 104–106 |
| 2.061 | NHNH₂ | Cl | CH₂—CH₂—OC₂H₅ | |
| 2.062 | NHNH₂ | Cl | CH₂—CH₂—O-n-C₃H₇ | |
| 2.063 | NHNH₂ | Cl | CH₂—CH₂—CH₂—OCH₃ | |
| 2.064 | NH₂ | Cl | 3-oxetanyl | |
| 2.065 | NHNH₂ | Cl | 3-oxetanyl | |

TABLE 2-continued

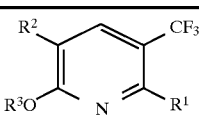   Ib

| No. | R¹ | R² | R³ | m.p. (0° C.), $n_D^{25}$, ¹H NMR (ppm), |
|---|---|---|---|---|
| 2.066 | NH₂ | Cl | CH₂—CH₂—CO₂H | |
| 2.067 | NH₂ | Cl | CH(CH₃)—CO₂H | |
| 2.068 | NH₂ | Cl | CH₂—CH₂—CH₂—CO₂H | |
| 2.069 | NHNH₂ | Cl | CH₂—CH₂—CO₂H | |
| 2.070 | NHNH₂ | Cl | CH(CH₃)—CO2H | |
| 2.071 | NHNH₂ | Cl | CH₂—CH₂—CH₂—CO₂H | |
| 2.072 | NH₂ | Cl | CH₂—CO₂CH₃ | |
| 2.073 | NH₂ | Cl | CH₂—CO₂C₂H₅ | |
| 2.074 | NH₂ | Cl | CH₂-CO₂-n-C₃H₇ | |
| 2.075 | NH₂ | Cl | CH₂CO₂-n-C₄H₉ | |
| 2.076 | NH₂ | Cl | CH₂CO₂-n-C₅H₁₁ | |
| 2.077 | NH₂ | Cl | CH(CH₃)—CO₂CH₃ | |
| 2.078 | NH₂ | Cl | CH(CH₃)—CO₂C₂H₅ | |
| 2.079 | NH₂ | Cl | CH(CH₃)—CO₂-n-C₃H₇ | |
| 2.080 | NHNH₂ | Cl | CH₂—CO₂CH₃ | 144–148 |
| 2.081 | NHNH₂ | Cl | CH₂—CO₂C₂H₅ | |
| 2.082 | NHNH₂ | Cl | CH₂—CO₂-n-C₃H₇ | |
| 2.083 | NHNH₂ | Cl | CH₂—CO₂-n-C₄H₉ | |
| 2.084 | NHNH₂ | Cl | CH₂—CO₂-n-C₅H₁₁ | |
| 2.085 | NHNH₂ | Cl | CH(CH₃)—CO₂CH₃ | |
| 2.086 | NHNH₂ | Cl | CH(CH₃)—CO₂C₂H₅ | |
| 2.087 | NHNH₂ | Cl | CH(CH₃)—CO₂-n-C₃H₇ | |
| 2.088 | NH₂ | Cl | CH₂—CO₂—CH₂—CH₂—OCH₃ | |
| 2.089 | NH₂ | Cl | CH₂—CO₂—CH₂—CH2—OC₂H₅ | |
| 2.090 | NH₂ | Cl | CH(CH₃)—CO₂—CH₂—CH₂—OCH₃ | |
| 2.091 | NH₂ | Cl | CH(CH₃)—CO₂—CH₂—CH₂—C₂H₅ | |
| 2.092 | NHNH₂ | Cl | CH₂—CO₂—CH₂—CH₂—OCH₃ | |
| 2.093 | NHNH₂ | Cl | CH₃—CO₂—CH₂—CH₂—OC₂H₅ | |
| 2.094 | NHNH₂ | Cl | CH(CH₃)—CO₂—CH₂—CH₂—OCH₃ | |
| 2.095 | NHNH₂ | Cl | CH(CH₃)—CO₂—CH₂—CH₂—OC₂H₅ | |
| 2.096 | NH₂ | Cl | CH₂—CO—NH—CH₃ | |
| 2.097 | NH₂ | Cl | CH₂—CO—NH—C₂H₅ | |
| 2.098 | NH₂ | Cl | CH₂—CO—NH-n-C₃H₇ | |
| 2.099 | NH₂ | Cl | CH₂—CO—NH-i-C₃H₇ | |
| 2.100 | NH₂ | Cl | CH₂—CO—NH-n-C₄H₉ | |
| 2.101 | NHNH₂ | Cl | CH₂—CO—NH—CH₃ | |
| 2.102 | NHNH₂ | Cl | CH₂—CO—NH—C₂H₅ | |
| 2.103 | NHNH₂ | Cl | CH₂—CO—NH-n-C₃H₇ | |
| 2.104 | NHNH₂ | Cl | CH₂—CO—NH-i-C₃H₇ | |
| 2.105 | NHNH₂ | Cl | CH₂—CO—NH-n-C₄H₉ | |
| 2.106 | NH₂ | Cl | CH(CH₃)—CO—NH—CH₃ | |
| 2.107 | NH₂ | Cl | CH(CH₃)—CO—NH—C₂H₅ | |
| 2.108 | NH₂ | Cl | CH(CH₃)—CO—NH-n-C₃H₇ | |
| 2.109 | NH₂ | Cl | CH(CH₃)—CO—NH-i-C₃H₇ | |
| 2.110 | NH₂ | Cl | CH(CH₃)—CO—NH-n-C₄H₉ | |
| 2.111 | NHNH₂ | Cl | CH(CH₃)—CO—NH—CH₃ | |
| 2.112 | NHNH₂ | Cl | CH(CH₃)—CO—NH—C₂H₅ | |
| 2.113 | NHNH₂ | Cl | CH(CH₃)—CO—NH-n-C₃H₇ | |
| 2.114 | NHNH₂ | Cl | CH(CH₃)—CO—NH-i-C₃H₇ | |
| 2.115 | NHNH₂ | Cl | CH(CH₃)—CO—NH-n-C₄H₉ | |
| 2.116 | NH₂ | Cl | CH₂—CO—N(CH₃)₂ | |
| 2.117 | NH₂ | Cl | CH₂—CO—N(CH₃)—C₂H₅ | |
| 2.118 | NH₂ | Cl | CH₂—CO—N(C₂H₅)₂ | |
| 2.119 | NH₂ | Cl | CH₂—CO—N(n-C₃H₇)₂ | |
| 2.120 | NHNH₂ | Cl | CH₂—CO—N(CH₃)₂ | |
| 2.121 | NHNH₂ | Cl | CH₂—CO—N(CH₃)—C₂H₅ | |
| 2.122 | NHNH₂ | Cl | CH₂—CO—N(C₂H₅)₂ | |
| 2.123 | NHNH₂ | Cl | CH₂—CO—N(n-C₃H₇)₂ | |
| 2.124 | NH₂ | Cl | CH(CH₃)—CO—N(CH₃)₂ | |
| 2.125 | NH₂ | Cl | CH(CH₃)—CO—N(CH₃)—C₂H₅ | |
| 2.126 | NH₂ | Cl | CH(CH₃)—CO—N(C₂H₅)₂ | |
| 2.127 | NH₂ | Cl | CH(CH₃)—CO—N(n-C₃H₇)₂ | |
| 2.128 | NHNH₂ | Cl | CH(CH₃)—CO—N(CH₃)₂ | |
| 2.129 | NHNH₂ | Cl | CH(CH₃)—CO—N(CH₃)₂—C₂H₅ | |
| 2.130 | NHNH₂ | Cl | CH(CH₃)—CO—N(C₂H₅)₂ | |
| 2.131 | NHNH₂ | Cl | CH(CH₃)—CO—N(n-C₃H₇)₂ | |
| 2.132 | NH₂ | Cl | CH₂—CO—NH—CH═CH₂ | |
| 2.133 | NH₂ | Cl | CH₂—CO—NH—CH₂—CH═CH₂ | |
| 2.134 | NHNH₂ | Cl | CH₂—CO—NH—CH═CH₂ | |

TABLE 2-continued $$\text{R}^3\text{O}-\underset{\text{N}}{\overset{\text{R}^2}{\bigcirc}}-\text{R}^1 \quad \text{with CF}_3 \text{ substituent} \quad Ib$$

| No. | R¹ | R² | R³ | m.p. (0° C.), $\eta_D^{25}$, ¹H NMR (ppm), |
|---|---|---|---|---|
| 2.135 | NHNH₂ | Cl | CH₂—CO—NH—CH₂—CH=CH₂ | |
| 2.136 | NH₂ | Cl | CH(CH₃)—CO—NH—CH=CH₂ | |
| 2.137 | NH₂ | Cl | CH(CH₃)—CO—NH—CH₂—CH=CH₂ | |
| 2.138 | NHNH₂ | Cl | CH(CH₃)—CO—NH—CH=CH₂ | |
| 2.139 | NHNH₂ | Cl | CH(CH₃)—CO—NH—CH₂—CH=CH₂ | |
| 2.140 | NH₂ | Cl | CH₂—CO—NH—CH₂—C≡CH | |
| 2.141 | NH₂ | Cl | CH(CH₃)—CO—NH—CH₂—C≡CH | |
| 2.142 | NHNH₂ | Cl | CH₂—CO—NH—CH₂—C≡CH | |
| 2.143 | NHNH₂ | Cl | CH(CH₃)—CO—NH—CH₂—C≡CH | |
| 2.144 | NH₂ | Cl | CH₂—CO—N(CH₃)CH₂—CH=CH₂ | |
| 2.145 | NH₂ | Cl | CH(CH₃)—CO—N(CH₃)—CH₂—CH=CH₂ | |
| 2.146 | NHNH₂ | Cl | CH₂—CO—N(CH₃)—CH₂—CH=CH₂ | |
| 2.147 | NHNH₂ | Cl | CH(CH₃)—CO—N(CH₃)—CH₂—CH=CH₂ | |
| 2.148 | NH₂ | Cl | CH₂—CO—N(CH₃)—CH₂—C≡CH | |
| 2.149 | NH₂ | Cl | CH(CH₃)—CO—N(CH₃)—CH₂—C≡CH | |
| 2.150 | NH₂ | Cl | CH₂—CO—N(CH₃)—CH₂—C≡CH | |
| 2.151 | NHNH₂ | Cl | CH(CH₃)—CO—N(CH₃)—CH₂—C≡CH | |
| 2.152 | NH₂ | Cl | CH₂—CH₂—O—N=C(CH₃)—CH₃ | |
| 2.153 | NHNH₂ | Cl | CH₂—CH₂—O—N=C(CH₃)—CH₃ | |
| 2.154 | NH₂ | Cl | CH₂-cyclopropyl | |
| 2.155 | NHNH₂ | Cl | CH₂-cyclopropyl | |
| 2.156 | NH₂ | Cl | NH—CH₃ | |
| 2.157 | NH₂ | Cl | NH—C₂H₅ | |
| 2.158 | NH₂ | Cl | NH-n-C₃H₇ | |
| 2.159 | NHNH₂ | Cl | NH—CH₃ | |
| 2.160 | NHNH₂ | Cl | NH—C₂H₅ | |
| 2.161 | NHNH₂ | Cl | NH-n-C₃H₇ | |
| 2.162 | NH₂ | Cl | N(CH₃)₂ | |
| 2.163 | NH₂ | Cl | N(CH₃)—C₂H₅ | |
| 2.164 | NH₂ | Cl | N(C₂H₅)₂ | |
| 2.165 | NHNH₂ | Cl | N(CH₃)₂ | |
| 2.166 | NHNH₂ | Cl | N(CH₃)—C₂H₅ | |
| 2.167 | NHNH₂ | Cl | N(C₂H₅)₂ | |
| 2.168 | NH₂ | Cl | N=CH—CH₃ | |
| 2.169 | NH₂ | Cl | N=CH—C₂H₅ | |
| 2.170 | NH₂ | Cl | N=CH-n-C₃H₇ | |
| 2.171 | NHNH₂ | Cl | N=CH—CH₃ | |
| 2.172 | NHNH₂ | Cl | N=CH—C₂H₅ | |
| 2.173 | NHNH₂ | Cl | N=CH-n-C₃H₇ | |
| 2.174 | NH₂ | Cl | N=C(CH₃)—CH₃ | |
| 2.175 | NH₂ | Cl | N=C(CH₃)—C₂H₅ | |
| 2.176 | NHNH₂ | Cl | N=C(CH₃)—CH₃ | |
| 2.177 | NHNH₂ | Cl | N=C(CH₃)—C₂H₅ | |
| 2.178 | NHNH₂ | Cl | C(CH₃)—C≡CH | |
| 2.179 | NHNH₂ | Cl | CH₂—C≡C—CH₃ | |
| 2.180 | NHNH₂ | Cl | CH₂—C≡C—CH₂Cl | |
| 2.181 | NH₂ | Cl | CH₂CO₂H | |
| 2.182 | NHNH₂ | Cl | CH₂CO₂H | |
| 2.183 | NH₂ | Cl | CH₂—CO—NH₂ | 144–146 |

TABLE 3

$$\text{Structure Ib: pyridine with } R^3 \text{ at 5-position, } CF_3 \text{ at 3-position, } R^3O \text{ at 6-position, } R^1 \text{ at 2-position}$$

| No. | $R^1$ | $R^2$ | $R^3$ | m.p. (0° C.), $\eta_D^{25}$, $^1$H NMR (ppm) |
|---|---|---|---|---|
| 3.001 | Cl | Cl | $CH_3$ | $\eta_D^{24} = 1.4890$ |
| 3.002 | Cl | Cl | $C_2H_5$ | $\eta_D^{23} = 1.4835$ |
| 3.003 | Cl | Cl | n-$C_3H_7$ | $\eta_D^{23} = 1.4808$ |
| 3.004 | Cl | Cl | i-$C_3H_7$ | $\eta_D^{23} = 1.4760$ |
| 3.005 | Cl | Cl | n-$C_4H_9$ | |
| 3.006 | Cl | Cl | i-$C_4H_9$ | |
| 3.007 | Cl | Cl | sec-$C_4H_9$ | |
| 3.008 | Cl | Cl | $CH_2-CH(CH_3)_2$ | |
| 3.009 | Cl | Cl | n-$C_5H_{11}$ | |
| 3.010 | Cl | Cl | n-$C_6H_{13}$ | |
| 3.011 | F | Cl | $CH_3$ | $\eta_D^{23} = 1.4504$ |
| 3.012 | F | Cl | $C_2H_5$ | $\eta_D^{23} = 1.4662$ |
| 3.013 | F | Cl | n-$C_3H_7$ | |
| 3.014 | F | Cl | i-$C_3H_7$ | $\eta_D^{23} = 1.4468$ |
| 3.015 | F | Cl | n-$C_4H_9$ | |
| 3.016 | F | Cl | i-$C_4H_9$ | |
| 3.017 | F | Cl | sec.-$C_4H_9$ | |
| 3.018 | F | Cl | $CH_2-CH(CH_3)_2$ | |
| 3.019 | F | Cl | n-$C_5H_{11}$ | |
| 3.020 | F | Cl | n-$C_6H_{13}$ | |
| 3.021 | Cl | Cl | $CH=CH_2$ | |
| 3.022 | Cl | Cl | $C(CH_3)=CH_2$ | |
| 3.023 | Cl | Cl | $CH_2-CH=CH_2$ | |
| 3.024 | Cl | Cl | $CH_2-C(CH_3)=CH_2$ | |
| 3.025 | Cl | Cl | $CH_2-CH=CH-CH_3$ | |
| 3.026 | Cl | Cl | $CH_2-CH=CHCl$ | |
| 3.027 | Cl | Cl | $CH_2-C(Cl)=CH_2$ | |
| 3.028 | F | Cl | $CH=CH_2$ | |
| 3.029 | F | Cl | $C(CH_3)=CH_2$ | |
| 3.030 | F | Cl | $CH_2-CH=CH_2$ | |
| 3.031 | F | Cl | $CH_2-C(CH_3)=CH_2$ | |
| 3.032 | F | Cl | $CH_2-CH=CH-CH_3$ | |
| 3.033 | F | Cl | $CH_2-CH=CHCl$ | |
| 3.034 | F | Cl | $CH_2-C(Cl)=CH_2$ | |
| 3.035 | Cl | Cl | $CH_2-C\equiv CH$ | $\eta_D^{24} = 1.5038$ |
| 3.036 | F | Cl | $CH_2-C\equiv CH$ | $\eta_D^{24} = 1.4732$ |
| 3.037 | Cl | Cl | $CH(CH_3)-C\equiv CH$ | |
| 3.038 | Cl | Cl | $CH_2-C\equiv C-CH_3$ | |
| 3.039 | Cl | Cl | $CH_2-C\equiv C-CH_2Cl$ | |
| 3.040 | Cl | Cl | cyclopropyl | |
| 3.041 | Cl | Cl | cyclobutyl | |
| 3.042 | Cl | Cl | cyclopentyl | |
| 3.043 | Cl | Cl | cyclohexyl | |
| 3.044 | F | Cl | cyclopropyl | |
| 3.045 | F | Cl | cyclobutyl | |
| 3.046 | F | Cl | cyclopentyl | |
| 3.047 | F | Cl | cyclohexyl | |
| 3.048 | Cl | Cl | $CH_2CN$ | |
| 3.049 | Cl | Cl | $CH_2-CH_2CN$ | |
| 3.050 | Cl | Cl | $CH_2-CH_2-CH_2CN$ | |
| 3.051 | Cl | Cl | $CH(CH_3)-CH_2CN$ | |
| 3.052 | F | Cl | $CH_2CN$ | |
| 3.053 | F | Cl | $CH_2-CH_2CN$ | $\eta_D^{24} = 1.4708$ |
| 3.054 | F | Cl | $CH_2-CH_2-CH_2CN$ | |
| 3.055 | F | Cl | $CH(CH_3)-CH_2CN$ | |
| 3.056 | Cl | Cl | $CH_2-CH_2-OCH_3$ | |
| 3.057 | Cl | Cl | $CH_2-CH_2-OC_2H_5$ | |
| 3.058 | Cl | Cl | $CH_2-CH_2-O-n-C_3H_7$ | |
| 3.059 | Cl | Cl | $CH_2-CH_2-CH_2-OCH_3$ | |
| 3.060 | F | Cl | $CH_2-CH_2-OCH_3$ | $\eta_D^{24} = 1.4572$ |
| 3.061 | F | Cl | $CH_2-CH_2-OC_2H_5$ | |
| 3.062 | F | Cl | $CH_2-CH_2-O-n-C_3H_7$ | |
| 3.063 | F | Cl | $CH_2-CH_2-CH_2-OCH_3$ | |
| 3.064 | Cl | Cl | 3-oxetanyl | |
| 3.065 | F | Cl | 3-oxetanyl | |

TABLE 3-continued

Ib

Structure: pyridine with R³ at position 5, CF₃ at position 3, R³O at position 2-oxygen side, R¹ at position next to N.

| No. | $R^1$ | $R^2$ | $R^3$ | m.p. (0° C.), $\eta_D^{25}$, $^1$H NMR (ppm) |
|---|---|---|---|---|
| 3.066 | Cl | Cl | $CH_2-CH_2-CO_2H$ | |
| 3.067 | Cl | Cl | $CH(CH_3)-CO_2H$ | |
| 3.068 | Cl | Cl | $CH_2-CH_2-CH_2-CO_2H$ | |
| 3.069 | F | Cl | $CH_2-CH_2-CO_2H$ | |
| 3.070 | F | Cl | $CH(CH3)-CO2H$ | |
| 3.071 | F | Cl | $CH_2-CH_2-CH_2-CO_2H$ | |
| 3.072 | Cl | Cl | $CH_2-CO_2CH_3$ | |
| 3.073 | Cl | Cl | $CH_2-CO_2C_2H_5$ | |
| 3.074 | Cl | Cl | $CH_2-CO_2\text{-n-}C_3H_7$ | |
| 3.075 | Cl | Cl | $CH_2CO_2\text{-n-}C_4H_9$ | |
| 3.076 | Cl | Cl | $CH_2CO_2\text{-n-}C_5H_{11}$ | |
| 3.077 | Cl | Cl | $CH(CH_3)-CO_2CH_3$ | |
| 3.078 | Cl | Cl | $CH(CH_3)-CO_2C_2H_5$ | |
| 3.079 | Cl | Cl | $CH(CH_3)-CO_2\text{-n-}C_3H_7$ | |
| 3.080 | F | Cl | $CH_2-CO_2CH_3$ | 55–57 |
| 3.081 | F | Cl | $CH_2-CO_2C_2H_5$ | |
| 3.082 | F | Cl | $CH_2-CO_2\text{-n-}C_3H_7$ | |
| 3.083 | F | Cl | $CH_2-CO_2\text{-n-}C_4H_9$ | $\eta_D^{23} = 1.4500$ |
| 3.084 | F | Cl | $CH_2-CO_2\text{-n-}C_5H_{11}$ | |
| 3.085 | F | Cl | $CH(CH_3)-CO_2CH_3$ | |
| 3.086 | F | Cl | $CH(CH_3)-CO_2C_2H_5$ | |
| 3.087 | F | Cl | $CH(CH_3)-CO_2\text{-n-}C_3H_7$ | |
| 3.088 | Cl | Cl | $CH_2-CO_2-CH_2-CH_2-OCH_3$ | |
| 3.089 | Cl | Cl | $CH_2-CO_2-CH_2-CH_2-OC_2H_5$ | |
| 3.090 | Cl | Cl | $CH(CH_3)-CO_2-CH_2-CH_2-OCH_3$ | |
| 3.091 | Cl | Cl | $CH(CH_3)-CO_2-CH_2-CH_2-OC_2H_5$ | |
| 3.092 | F | Cl | $CH_2-CO_2-CH_2-CH_2-OCH_3$ | |
| 3.093 | F | Cl | $CH_2-CO_2-CH_2-CH_2-OC_2H_5$ | |
| 3.094 | F | Cl | $CH(CH_3)-CO_2-CH_2-CH_2-OCH_3$ | |
| 3.095 | F | Cl | $CH(CH_3)-CO_2-CH_2-CH_2-OC_2H_5$ | |
| 3.096 | Cl | Cl | $CH_2-CO-NH-CH_3$ | |
| 3.097 | Cl | Cl | $CH_2-CO-NH-C_2H_5$ | |
| 3.098 | Cl | Cl | $CH_2-CO-NH\text{-n-}C_3H_7$ | |
| 3.099 | Cl | Cl | $CH_2-CO-NH\text{-i-}C_3H_7$ | |
| 3.100 | Cl | Cl | $CH_2-CO-NH\text{-n-}C_4H_9$ | |
| 3.101 | F | Cl | $CH_2-CO-NH-CH_3$ | |
| 3.102 | F | Cl | $CH_2-CO-NH-C_2H_5$ | |
| 3.103 | F | Cl | $CH_2-CO-NH\text{-n-}C_3H_7$ | |
| 3.104 | F | Cl | $CH_2-CO-NH\text{-i-}C_3H_7$ | |
| 3.105 | F | Cl | $CH_2-CO-NH\text{-n-}C_4H_9$ | |
| 3.106 | Cl | Cl | $CH(CH_3)-CO-NH-CH_3$ | |
| 3.107 | Cl | Cl | $CH(CH_3)-CO-NH-C_2H_5$ | |
| 3.108 | Cl | Cl | $CH(CH_3)-CO-NH\text{-n-}C_3H_7$ | |
| 3.109 | Cl | Cl | $CH(CH_3)-CO-NH\text{-i-}C_3H_7$ | |
| 3.110 | Cl | Cl | $CH(CH_3)-CO-NH\text{-n-}C_4H_9$ | |
| 3.111 | F | Cl | $CH(CH_3)-CO-NH-CH_3$ | |
| 3.112 | F | Cl | $CH(CH_3)-CO-NH-C_2H_5$ | 151–153 |
| 3.113 | F | Cl | $CH(CH_3)-CO-NH\text{-n-}C_3H_7$ | |
| 3.114 | F | Cl | $CH(CH_3)-CO-NH\text{-i-}C_3H_7$ | |
| 3.115 | F | Cl | $CH(CH_3)-CO-NH\text{-n-}C_4H_9$ | |
| 3.116 | Cl | Cl | $CH_2-CO-N(CH_3)_2$ | |
| 3.117 | Cl | Cl | $CH_2-CO-N(CH_3)-C_2H_5$ | |
| 3.118 | Cl | Cl | $CH_2-CO-N(C_2H_5)_2$ | |
| 3.119 | Cl | Cl | $CH_2-CO-N(\text{n-}C_3H_7)_2$ | |
| 3.120 | F | Cl | $CH_2-CO-N(CH_3)_2$ | |
| 3.121 | F | Cl | $CH_2-CO-N(CH_3)-C_2H_5$ | |
| 3.122 | F | Cl | $CH_2-CO-N(C_2H_5)_2$ | |
| 3.123 | F | Cl | $CH_2-CO-N(\text{n-}C_3H_7)_2$ | |
| 3.124 | Cl | Cl | $CH(CH_3)-CO-N(CH_3)_2$ | |
| 3.125 | Cl | Cl | $CH(CH_3)-CO-N(CH_3)-C_2H_5$ | |
| 3.126 | Cl | Cl | $CH(CH_3)-CO-N(C_2H_5)_2$ | |
| 3.127 | Cl | Cl | $CH(CH_3)-CO-N(\text{n-}C_3H_7)_2$ | |
| 3.128 | F | Cl | $CH(CH_3)-CO-N(CH_3)_2$ | |
| 3.129 | F | Cl | $CH(CH_3)-CO-N(CH_3)-C_2H_5$ | |
| 3.130 | F | Cl | $CH(CH_3)-CO-N(C_2H_5)_2$ | |
| 3.131 | F | Cl | $CH(CH_3)-CO-N(\text{n-}C_3H_7)_2$ | |
| 3.132 | Cl | Cl | $CH_2-CO-NH-CH=CH_2$ | |
| 3.133 | Cl | Cl | $CH_2-CO-NH-CH_2-CH=CH_2$ | |
| 3.134 | F | Cl | $CH_2-CO-NH-CH=CH_2$ | |

TABLE 3-continued $$\text{structure Ib: pyridine with } R^3 \text{ at position 3, } CF_3 \text{ at position 5, } R^3O \text{ at position 2, } R^1 \text{ at position 6}$$

| No. | R$^1$ | R$^2$ | R$^3$ | m.p. (0° C.), $\eta_D^{25}$, $^1$H NMR (ppm) |
|---|---|---|---|---|
| 3.135 | F | Cl | CH$_2$—CO—NH—CH$_2$—CH=CH$_2$ | |
| 3.136 | Cl | Cl | CH(CH$_3$)—CO—NH—CH=CH$_2$ | |
| 3.137 | Cl | Cl | CH(CH$_3$)—CO—NH—CH$_2$—CH=CH$_2$ | |
| 3.138 | F | Cl | CH(CH$_3$)—CO—NH—CH=CH$_2$ | |
| 3.139 | F | Cl | CH(CH$_3$)—CO—NH—CH$_2$—CH=CH$_2$ | |
| 3.140 | Cl | Cl | CH$_2$—CO—NH—CH$_2$—C≡CH | |
| 3.141 | Cl | Cl | CH(CH$_3$)—CO—NH—CH$_2$—C≡CH | |
| 3.142 | F | Cl | CH$_2$—CO—NH—CH$_2$—C≡CH | |
| 3.143 | F | Cl | CH(CH$_3$)—CO—NH—CH$_2$—C≡CH | |
| 3.144 | Cl | Cl | CH$_2$—CO—N(CH$_3$)CH$_2$—CH=CH$_2$ | |
| 3.145 | Cl | Cl | CH(CH$_3$)—CO—N(CH$_3$)—CH$_2$—CH=CH$_2$ | |
| 3.146 | F | Cl | CH$_2$—CO—N(CH$_3$)CH$_2$—CH=CH$_2$ | |
| 3.147 | F | Cl | CH(CH$_3$)—CO—N(CH$_3$)—CH$_2$—CH=CH$_2$ | |
| 3.148 | Cl | Cl | CH$_2$—CO—N(CH$_3$)—CH$_2$—C≡CH | |
| 3.149 | Cl | Cl | CH(CH$_3$)—CO—N(CH$_3$)—CH$_2$—C≡CH | |
| 3.150 | F | Cl | CH$_2$—CO—N(CH$_3$)—CH$_2$—C≡CH | |
| 3.151 | F | Cl | CH(CH$_3$)—CO—N(CH$_3$)—CH$_2$—C≡CH | |
| 3.152 | Cl | Cl | CH$_2$—CH$_2$—O—N=C(CH$_3$)—CH$_3$ | |
| 3.153 | F | Cl | CH$_2$—CH$_2$—O—N=C(CH$_3$)—CH$_3$ | |
| 3.154 | Cl | Cl | CH$_2$-cyclopropyl | |
| 3.155 | F | Cl | CH$_2$-cyclopropyl | |
| 3.156 | Cl | Cl | NH—CH$_3$ | |
| 3.157 | Cl | Cl | NH—C$_2$H$_5$ | |
| 3.158 | Cl | Cl | NH-n-C$_3$H$_7$ | |
| 3.159 | F | Cl | NH—CH$_3$ | |
| 3.160 | F | Cl | NH—C$_2$H$_5$ | |
| 3.161 | F | Cl | NH-n-C$_3$H$_7$ | |
| 3.162 | Cl | Cl | N(CH$_3$)$_2$ | |
| 3.163 | Cl | Cl | N(CH$_3$)—C$_2$H$_5$ | |
| 3.164 | Cl | Cl | N(C$_2$H$_5$)$_2$ | |
| 3.165 | F | Cl | N(CH$_3$)$_2$ | |
| 3.166 | F | Cl | N(CH$_3$)—C$_2$H$_5$ | |
| 3.167 | F | Cl | N(C$_2$H$_5$)$_2$ | |
| 3.168 | Cl | Cl | N=CH—CH$_3$ | |
| 3.169 | Cl | Cl | N=CH—C$_2$H$_5$ | |
| 3.170 | Cl | Cl | N=CH-n-C$_3$H$_7$ | |
| 3.171 | F | Cl | N=CH—CH$_3$ | |
| 3.172 | F | Cl | N=CH—C$_2$H$_5$ | |
| 3.173 | F | Cl | N=CH-n-C$_3$H$_7$ | |
| 3.174 | Cl | Cl | N=C(CH$_3$)—CH$_3$ | |
| 3.175 | Cl | Cl | N=C(CH$_3$)—C$_2$H$_5$ | |
| 3.176 | F | Cl | N=C(CH$_3$)—CH$_3$ | 44–47 |
| 3.177 | F | Cl | N=C(CH$_3$)—C$_2$H$_5$ | |
| 3.178 | F | Cl | C(CH)$_3$—C≡CH | |
| 3.179 | F | Cl | CH$_2$—C≡C—CH$_3$ | |
| 3.180 | F | Cl | CH$_2$—C≡C—CH$_2$Cl | |
| 3.181 | Cl | Cl | CH$_2$CO$_2$H | |
| 3.182 | F | Cl | CH$_2$CO$_2$H | |

TABLE 4

$$\text{Structure: pyridine with } CF_3 \text{ at position 3, } R^2 \text{ at position 5, } R^1 \text{ at position 6, } OR^3 \text{ at position 2}$$  Ia

| No. | R¹ | R² | R³ | m.p. (° C.), $\eta_D^{25}$, ¹H NMR (ppm), |
|---|---|---|---|---|
| 4.001 | NH₂ | F | CH₃ | |
| 4.002 | NH₂ | F | C₂H₅ | |
| 4.003 | NH₂ | F | n-C₃H₇ | |
| 4.004 | NHNH₂ | F | CH₃ | |
| 4.005 | NHNH₂ | F | C₂H₅ | |
| 4.006 | NHNH₂ | F | n-C₃H₇ | |
| 4.007 | NH₂ | F | CH=CH₂ | |
| 4.008 | NH₂ | F | C(CH₃)=CH₂ | |
| 4.009 | NH₂ | F | CH₂—CH=CH₂ | |
| 4.010 | NH₂ | F | CH₂—CH=CHCl | |
| 4.011 | NHNH₂ | F | CH=CH₂ | |
| 4.012 | NHNH₂ | F | C(CH₃)=CH₂ | |
| 4.013 | NHNH₂ | F | CH₂—CH=CH₂ | |
| 4.014 | NHNH₂ | F | CH₂—CH=CHCl | |
| 4.015 | NH₂ | F | CH₂—C≡CH | |
| 4.016 | NHNH₂ | F | CH₂—C≡CH | |
| 4.017 | NH₂ | F | CH(CH₃)—C≡CH | |
| 4.018 | NH₂ | F | CH₂—C≡C—CH₂Cl | |
| 4.019 | NHNH₂ | F | C(CH₃)—C≡CH | |
| 4.020 | NHNH₂ | F | CH₂—C≡C—CH₂Cl | |
| 4.021 | NH₂ | F | cyclopropyl | |
| 4.022 | NHNH₂ | F | cyclopropyl | |
| 4.023 | NH₂ | F | CH₂CN | |
| 4.024 | NH₂ | F | CH₂—CH₂CN | |
| 4.025 | NHNH₂ | F | CH₂CN | |
| 4.026 | NHNH₂ | F | CH₂—CH₂CN | |
| 4.027 | NH₂ | F | CH₂—CH₂OCH₃ | |
| 4.028 | NHNH₂ | F | CH₂—CH₂OCH₃ | |
| 4.029 | NH₂ | F | 3-oxetanyl | |
| 4.030 | NHNH₂ | F | 3-oxetanyl | |
| 4.031 | NH₂ | F | CH₂—CO₂H | |
| 4.032 | NH₂ | F | CH₂—CH₂—CO₂H | |
| 4.033 | NH₂ | F | CH(CH₃)CO₂H | |
| 4.034 | NHNH₂ | F | CH₂—CO₂H | |
| 4.035 | NHNH₂ | F | CH₂—CH₂—CO₂H | |
| 4.036 | NHNH₂ | F | CH(CH₃)CO₂H | |
| 4.037 | NH₂ | F | CH₂—CO₂CH₃ | |
| 4.038 | NH₂ | F | CH₂—CO₂C₂H₅ | |
| 4.039 | NH₂ | F | CH₂—CO₂-n-C₅H₁₁ | |
| 4.040 | NHNH₂ | F | CH₂—CO₂CH₃ | |
| 4.041 | NHNH₂ | F | CH₂—CO₂C₂H₅ | |
| 4.042 | NHNH₂ | F | CH₂—CO₂-n-C₅H₁₁ | |
| 4.043 | NH₂ | F | CH(CH₃)CO₂CH₃ | |
| 4.044 | NHNH₂ | F | CH(CH₃)CO₂CH₃ | |
| 4.045 | NH₂ | F | CH₂—CO₂—CH₂—CH₂OCH₃ | |
| 4.046 | NHNH₂ | F | CH₂—CO₂—CH₂—CH₂OCH₃ | |
| 4.047 | NH₂ | F | CH₂—CO—NH—CH₃ | |
| 4.048 | NH₂ | F | CH₂—CO—NH—C₂H₅ | |
| 4.049 | NHNH₂ | F | CH₂—CO—NH—CH₃ | |
| 4.050 | NHNH₂ | F | CH₂—CO—NH—C₂H₅ | |
| 4.051 | NH₂ | F | CH(CH₃)CO—NHCH₃ | |
| 4.052 | NHNH₂ | F | CH(CH₃)CO—NHCH₃ | |
| 4.053 | NH₂ | F | CH₂—CO—N(CH₃)₂ | |
| 4.054 | NHNH₂ | F | CH₂—CO—N(CH₃)₂ | |
| 4.055 | NH₂ | F | CH(CH₃)CO—N(CH₃)₂ | |
| 4.056 | NHNH₂ | F | CH(CH₃)CO—N(CH₃)₂ | |
| 4.057 | NH₂ | F | CH₂—CO—NH—CH₂—CH=CH₂ | |
| 4.058 | NHNH₂ | F | CH₂—CO—NH—CH₂—CH=CH₂ | |
| 4.059 | NH₂ | F | CH(CH₃)CO—NH—CH₂—CH=CH₂ | |
| 4.060 | NHNH₂ | F | CH(CH₃)CO—NH—CH₂—CH=CH₂ | |
| 4.061 | NH₂ | F | CH₂—CO—NH—CH₂—C≡CH | |
| 4:062 | NHNH₂ | F | CH₂—CO—NH—CH₂—C≡CH | |

TABLE 4-continued

Ia $$\begin{array}{c} CF_3 \diagdown \diagup R^2 \\ R^3O \diagup N \diagdown R^1 \end{array}$$

| No. | R¹ | R² | R³ | m.p. (0° C.), $\eta_D^{25}$, ¹H NMR (ppm), |
|---|---|---|---|---|
| 4.063 | NH₂ | F | CH(CH₃)CO—NH—CH₂—C≡CH | |
| 4.064 | NHNH₂ | F | CH(CH₃)CO—NH—CH₂—C≡CH | |
| 4.065 | NH₂ | F | CH₂—CO—N(CH₃)—CH₂—CH=CH₂ | |
| 4.066 | NHNH₂ | F | CH₂—CO—N(CH₃)CH₂—CH=CH₂ | |
| 4.067 | NH₂ | F | CH₂—CO—N(CH₃)CH₂—C≡CH | |
| 4.068 | NHNH₂ | F | CH₂—CO—N(CH₃)CH₂—C≡CH | |
| 4.069 | NH₂ | F | CH₂—CH₂—O—N=C(CH₃)—CH₃ | |
| 4.070 | NHNH₂ | F | CH₂—CH₂—O—N=C(CH₃)—CH₃ | |
| 4.071 | NH₂ | F | NH₂-cyclopropyl | |
| 4.072 | NHNH₂ | F | NH₂-cyclopropyl | |
| 4.073 | NH₂ | F | NH—CH₃ | |
| 4.074 | NH₂ | F | NH—C₂H₅ | |
| 4.075 | NHNH₂ | F | NH—CH₃ | |
| 4.076 | NHNH₂ | F | NH—C₂H₅ | |
| 4.077 | NH₂ | F | N(CH₃)₂ | |
| 4.078 | NH₂ | F | N(CH₃)—C₂H₅ | |
| 4.079 | NHNH₂ | F | N(CH₃)₂ | |
| 4.080 | NHNH₂ | F | N(CH₃)—C₂H₅ | |
| 4.081 | NH₂ | F | N=CH—CH₃ | |
| 4.082 | NH₂ | F | N=CH—C₂H₅ | |
| 4.083 | NHNH₂ | F | N=CH—CH₃ | |
| 4.084 | NHNH₂ | F | N=CH—C₂H₅ | |
| 4.085 | NH₂ | F | N=C(CH₃)—CH₃ | |
| 4.086 | NHNH₂ | F | N=C(CH₃)—CH₃ | |

Examples of 1-(pyridyl)pyrazoles:

EXAMPLE IV.1

5-Amino-4-cyano-1-[3-chloro-6-fluoro-5-trifluoromethylpyrid-2-yl]pyrazole 12.2 g [0.1 mol] of ethoxymethylenemalonitrile were added in the course of 5 minutes at 22° C. with stirring to 23 g [0.1 mol] of 3-chloro-6-fluoro-2-hydrazino-5-trifluoromethylpyridine in 200 ml of ethanol and stirring was continued for 8 hours at 78° C. The precipitate which had separated out was filtered off with suction and partitioned in water/methylene chloride. The organic phase was dried over magnesium sulfate and filtered with suction through neutral aluminum oxide. The filtrate was concentrated, stirred with ether/pentane 1:1, filtered off with suction and dried, giving 12.6 g [41% of theory] of the title compound of m.p. 156°–159° C. [active ingredient example No. 5.019].

EXAMPLE IV.2

5-Amino-4-cyano-1-[5-chloro-6-methoxy-3-trifluoromethylpyrid-2-yl]pyrazole 4.7 g [0.0385 mol] of ethoxymethylenemalonitrile were added in the course of 5 minutes at 22° C. with stirring to 9.3 g [0.0385 mol] of 3-chloro-6-hydrazino-2-methoxy-5-trifluoromethylpyridine in 200 ml of ethanol and stirring was continued for 8 hours at 78° C. The reaction solution was concentrated, stirred with water and filtered with suction, the solid was dissolved in methylene chloride, and the mixture was purified using active charcoal, dried and filtered with suction through silica gel. After concentration in vacuo, stirring with ether/pentane 1:1, filtration with suction and drying, 9.1 g [74% of theory] of the title compound of m.p. 163°–165° C. were obtained [active ingredient example No. 6.001].

EXAMPLE IV.3

5-Amino-4-cyano-1-(3-chloro-6-methoxy-5-trifluoromethylpyrid-2-yl)pyrazole 5 ml of methanol were added in the course of 10 minutes at 20° C. to a suspension of 0.23 g (0.0092 mol) of 95% sodium hydride in 75 ml of methyl tert-butyl ether and the mixture was stirred for 25 minutes until a clear solution was obtained. 3 g (0.0098 mol) of 5-amino-4-cyano-1-(3-chloro-6-fluoro-5-trifluoromethylpyrid-2-yl)pyrazole (Example IV.1.) in 50 ml of methyl tert-butyl ether were subsequently added with stirring and the mixture was stirred for 2 hours at 25° C. Approximately 50 g of ice and 100 ml of hydrochloric acid were added and the phases were separated. The organic phase was washed using saturated sodium chloride solution, dried and filtered through silica gel. After concentration, stirring with ether/pentane, filtration with suction and drying, 2.4 g (77% of theory) of the title compound of m.p. 135°–139° C. were obtained (active ingredient example No. 5.003).

EXAMPLE IV.4

Ethyl 5-amino-1-(5-chloro-6-propargyloxy-3-trifluoromethylpyrid-2-yl)pyrazole-4-carboxylate 19.1 g (0.113 mol) of ethyl ethoxymethylenecyanoacetate were added with stirring in the course of 10 minutes to a mixture of 30 g (0.113 mol) of 5-chloro-6-propargyloxy-3-trifluoromethylpyridyl-2-hydrazine and 300 ml of methyl glycol and the mixture was stirred for 30 minutes at 80° C. After the reaction mixture had been stirred for a further 4 hours at 120° C., it was concentrated in vacuo and stirred in ether/pentane. After filtration with suction, 36.1 g (82.2% of theory) of the title compound of m.p. 118°–119° C. were obtained (active ingredient example No. 6.003).

Other compounds VIII which were prepared by methods similar to those given in the Examples or which can be prepared either by the processes described above or by methods known per se are listed in the tables which follow.

TABLE 5

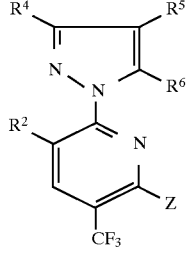

VIIIa

| No. | R² | R⁴ | R⁵ | R⁶ | Z | m.p. °C., $n_D^{23}$, $^1$H NMR[CDCl₃/TMS]δ |
|---|---|---|---|---|---|---|
| 5.001 | Cl | H | NO₂ | NH₂ | OCH₃ | 143–145 |
| 5.002 | Cl | H | NO₂ | Br | OCH₃ | 83–86 |
| 5.003 | Cl | H | CN | NH₂ | OCH₃ | 135–139 |
| 5.004 | Cl | H | CO₂C₂H₅ | NH₂ | O—CH₂—C≡CH | 185–186 |
| 5.005 | Cl | H | NO₂ | NH—C(=O)—C₂H₅ | F | 136–138 |
| 5.006 | Cl | H | CN | NH₂ | O—CH₂—C≡CH | 194–196 |
| 5.007 | Cl | H | CO₂C₂H₅ | NH₂ | OCH₃ | 165–166 |
| 5.008 | Cl | H | CO₂C₂H₅ | Br | O—CH₂—C≡CH | 1.5440 |
| 5.009 | Cl | H | NO₂ | NH₂ | O—CH₂—C≡CH | 208–210 |
| 5.010 | Cl | H | NO₂ | NH—C(=O)—C₂H₅ | OCH₃ | 127–128 |
| 5.011 | Cl | H | CN | NH₂ | O—CH(CH₃)—CO₂C₂H₅ | 175–177 |
| 5.012 | Cl | H | CO₂C₂H₅ | NH₂ | O—CH₂CO₂CH₃ | 129–131 |
| 5.013 | Cl | H | CO₂C₂H₅ | NH₂ | O—CH(CH₃)—CO₂CH₃ | 114–118 |
| 5.014 | Cl | H | CN | N[C(=O)CH₃]₂ | F | 146–150 |
| 5.015 | Cl | H | SCN | N[C(=O)CH₃]₂ | F | 135–136 |
| 5.016 | Cl | H | CN | NH₂ | O—C₂H₅ | 179–180 |
| 5.017 | Cl | H | CN | NH₂ | O-i-C₃H₇ | 182–183 |
| 5.018 | Cl | H | SCN | NH₂ | F | 109–114 |
| 5.019 | Cl | H | CN | NH₂ | F | 156–159 |
| 5.020 | Cl | H | NO₂ | NH—CH₂—CH=CH₂ | Cl | 118–121 |
| 5.021 | Cl | H | NO₂ | NH₂ | F | 129–130 |
| 5.022 | Cl | H | NO₂ | NH₂ | Cl | 125–128 |
| 5.023 | Cl | H | NO₂ | NH—CH₂—C≡CH | Cl | 105–108 |
| 5.024 | Cl | H | NO₂ | Br | F | resin, pyraz. 8.44 (s/1), pyrid. 8.39 (d/1) |
| 5.025 | Cl | H | NO₂ | Br | Cl | 97–99 |
| 5.026 | Cl | H | NO₂ | NH—C(=O)—CH₃ | Cl | 161–162 |
| 5.027 | Cl | H | NO₂ | NH—C(=O)—CH₃ | F | 104–106 |

TABLE 5-continued

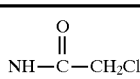

| No. | R² | R⁴ | R⁵ | R⁶ | Z | m.p. °C., $n_D^{23}$, ¹H NMR[CDCl₃/TMS]δ |
|---|---|---|---|---|---|---|
| 5.028 | Cl | H | NO₂ | NH—C(=O)—CH₂Cl | Cl | 157–159 |
| 5.029 | Cl | H | NO₂ | NH—C(=O)—CF₃ | F | 102–103 |
| 5.030 | Cl | H | NO₂ | NH—C(=O)—CF₃ | Cl | 99–101 |
| 5.031 | Cl | H | Cl | NH₂ | Cl | 150–151 |
| 5.032 | Cl | H | Cl | NH—C(=O)—CH | Cl | 182–184 |
| 5.033 | Cl | H | Cl | NH—C(=O)—CH₂Cl | F | 129–131 |
| 5.034 | Cl | H | Cl | NH—C(=O)—CH₂Cl | Cl | 156–158 |
| 5.035 | Cl | H | SCN | NH₂ | Cl | 122–125 |
| 5.036 | F | H | CN | Br | Cl | 55–56 |
| 5.037 | Cl | H | NO₂ | NH₂ | Br | 143–145 |
| 5.038 | Cl | H | NO₂ | NH—C₃H₅ | Br | 128–129 |
| 5.039 | Cl | H | NO₂ | NH—C₂H₅ | Br | 185–186 |
| 5.040 | Cl | H | NO₂ | NH—C(=O)—C₂H₅ | Br | 153–155 |
| 5.041 | Cl | H | Cl | NH₂ | Br | 133–135 |
| 5.042 | Cl | H | CO₂CH₃ | NH₂ | Cl | 183–185 |
| 5.043 | Cl | H | NO₂ | Br | Br | 105–106 |
| 5.044 | Cl | H | Br | NH₂ | Br | 133–135 |

TABLE 6

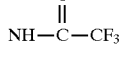

| No. | R² | R⁴ | R⁵ | R⁶ | Z | m.p. °C., $n_D^{23}$, ¹H NMR[CDCl₃/TMS]δ |
|---|---|---|---|---|---|---|
| 6.001 | Cl | H | CN | NH₂ | OCH₃ | 163–165 |
| 6.002 | Cl | H | CO₂C₂H₅ | NH₂ | OCH₃ | 95–98 |
| 6.003 | Cl | H | CO₂C₂H₅ | NH₂ | O—CH₂—C≡CH | 118–119 |

TABLE 6-continued

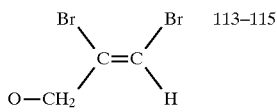

| No. | R² | R⁴ | R⁵ | R⁶ | Z | m.p. °C., $n_D^{23}$, $^1H$ NMR[CDCl$_3$/TMS]δ |
|---|---|---|---|---|---|---|
| 6.004 | Cl | H | CN | NH$_2$ | O—CH$_2$—C≡CH | 180–182 |
| 6.005 | Cl | H | CN | Br |  | 113–115 |
| 6.006 | Cl | H | NO$_2$ | NH$_2$ | OCH$_3$ | 192 |
| 6.007 | Cl | H | NO$_2$ | NH—C(=O)—CH$_3$ | OCH$_3$ | 190–195 |

The compounds I and their agriculturally useful salts are suitable as herbicides, both in the form of mixtures of isomers and as pure isomers. The herbicides comprising I provide very effective control of plant growth on uncultivated areas, particularly at high rates of application. They act against broad-leaved weeds and grass weeds in crops such as wheat, rice, maize, soybeans and cotton without significantly damaging the crop plants. This effect is particularly pronounced at low rates of application.

Depending on the particular application method, the compounds I, or compositions comprising them, can additionally be used in a further number of crop plants for eliminating undesirable plants. Suitable crops are, for example, the following: *Allium cepa, Ananas comosus, Arachis hypogaea, Asparagus officinalis, Beta vulgaris* ssp. altissima, *Beta vulgaris* ssp. rapa, *Brassica napus* var. napus, *Brassica napus* var. napobrassica, *Brassica rapa* var. silvestris, *Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spp., *Manihot esculenta, Medicago sativa,* Musa spp., *Nicotiana tabacum* (*N. rustica*), *Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera, Zea mays.*

In addition, the compounds I can also be used in crops which are tolerant against the action of herbicides due to breeding, including genetic engineering methods.

The herbicidal compositions or the active ingredients can be applied pre- or postemergence. If the active ingredients are less well tolerated in certain crop plants, application techniques may be used in which the herbicidal compositions are sprayed, with the aid of the spraying equipment, in such a way that they come into as little contact as possible with the leaves of the sensitive crop plants while reaching the leaves of undesirable plants growing underneath, or the naked soil surface (post-directed, lay-by).

The compounds I, or the herbicidal compositions comprising them, can be applied, for example, in the form of directly sprayable aqueous solutions, powders, suspensions, also highly concentrated aqueous, oily or other suspensions or dispersions, emulsions, oil dispersions, pastes, dusts, materials for spreading, or granules, by means of spraying, atomizing, dusting, scattering or pouring. The use forms depend on the intended purposes; in any case, they should guarantee the finest possible distribution of the active ingredients according to the invention.

Suitable inert additives are in the main: mineral oil fractions of medium to high boiling point, such as kerosene or diesel oil, furthermore coal tar oils and oils of vegetable or animal origin, aliphatic, cyclic and aromatic hydrocarbons, eg. paraffins, tetrahydro-naphthalene, alkylated naphthalenes or their derivatives, alkylated benzenes and their derivatives, alcohols such as methanol, ethanol, propanol, butanol or cyclohexanol, ketones such as cyclohexanone, or strongly polar solvents, eg. amines such as N-methylpyrrolidone, or water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is also possible to prepare concentrates comprising active ingredient, wetting agent, tackifier, dispersant or emulsifier and, if desired, solvent or oil, and these concentrates are suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, or fatty acids, alkyl- and alkylarylsulfonates, alkyl, lauryl ether and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for spreading and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin, such as cereal meal, tree bark meal, wood meal and nutshell meal, cellulose powder, or other solid carriers.

The concentrations of the active ingredients I in the ready-to-use preparations can be varied within wide limits. In general, the formulations comprise from 0.001 to 98% by weight, preferably from 0.01 to 95% by weight, of active ingredient. The active ingredients are employed in a purity from 90% to 100%, preferably 95% to 100% (according to NMR spectrum).

The compounds I according to the invention can be formulated for example as follows:

I 20 parts by weight of Compound No. 5.001 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100 000 parts by weight of water and finely distributing it therein gives an aqueous dispersion comprising 0.02% by weight of the active ingredient.

II 20 parts by weight of Compound No. 5.002 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient.

III 20 parts by weight of the active ingredient No. 5.003 are dissolved in a mixture composed of 25 parts by weight of cyclohexanone, 65 parts by weight of a mineral oil fraction of boiling point 210° to 280° C. and 10 parts by weight of the adduct of 40 mol of ethylene oxide to 1 mol of castor oil. Pouring the solution into 100 000 parts by weight of water and finely distributing it therein gives an aqueous dispersion comprising 0.02% by weight of the active ingredient.

IV 20 parts by weight of the active ingredient No. 5.005 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20 000 parts by weight of water gives a spray mixture comprising 0.1% by weight of the active ingredient.

V 3 parts by weight of the active ingredient No. 5.010 are mixed with 97 parts by weight of finely divided kaolin. This gives a dust comprising 3% by weight of the active ingredient.

VI 20 parts by weight of the active ingredient No. 5.016 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of Compound No. 5.017 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII l part by weight of Compound No. 5.018 is dissolved in a mixture composed of 80 parts by weight of cyclohexanone and 20 parts by weight of Emulphor EL (ethoxylated castor oil). This gives a stable emulsion concentrate.

To widen the spectrum of action and to achieve synergistic effects, the substituted trifluoromethylpyridines I can be mixed with a large number of representatives of other groups of herbicidal or growth-regulating active ingredients and then applied concomitantly. Examples of suitable components for mixtures are 1,2,4-thiadiazoles, 1,3,4-thiadiazoles, amides, aminophosphoric acid and its derivatives, aminotriazoles, anilides, (het)aryloxyalkanoic acid and its derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- or heteroaryloxyphenoxypropionic acid esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, as a mixture with further crop protection agents, for example with pesticides or agents for controlling phytopathogenic fungi or bacteria. Also of interest is the miscibility with mineral salt solutions, which are employed for treating nutrient and trace element deficiencies. Nonphytotoxic oils and oil concentrates may also be added.

Depending on the intended purpose, the season, the target plants and the growth stage, the application rates of active ingredient are from 0.001 to 3.0, preferably 0.01 to 1.0, kg of active ingredient (a.i.) per ha.

Application examples

The herbicidal action of the substituted trifluoromethylpyridines of the formula I was demonstrated by greenhouse experiments:

The culture containers used were plastic flowerpots containing loamy sand with approximately 3.0% of humus as the substrate. The seeds of the test plants were sown separately for each species.

In the case of preemergence treatment, the active ingredients, which were suspended or emulsified in water, were applied directly after sowing by means of finely distributing nozzles. The containers were irrigated gently to promote germination and growth and subsequently covered with translucent plastic hoods until the plants had rooted. This cover resulted in uniform germination of the test plants, unless germination was adversely affected by the active ingredients.

For postemergence treatment, the test plants were first grown to a plant height of 3 to 15 cm, depending on the plant habit, and only then treated with the active ingredients which were suspended or emulsified in water. The test plants were either sown directly and grown in the same containers, or grown separately as seedlings and transplanted to the test containers a few days prior to treatment. The rate of application for the postemergence treatment was 0.0156 or 0.0078 kg of a.i. per ha.

The plants were kept at from 10°–25° C., or 20°–35° C., depending on the species. The test period extended to 2 to 4 weeks. During this time, the plants were tended, and their response to the individual treatments was evaluated.

They were assessed using a scale from 0 to 100. 100 means no emergence of the plants, or complete destruction of at least the aerial parts, and 0 means no damage or normal course of growth.

The plants used in the greenhouse experiments belonged to the following species:

| Scientific name | Common name |
| --- | --- |
| Glycine max | soybean |
| Abutilon theophrasti | velvetleaf |
| Solanum nigrum | black nightshade |

Comparison example

The compound according to the invention and the comparison product, which has been disclosed, were used postemergence in the greenhouse by the methods described above.

The comparison product used is:
A from DE 3 520 330

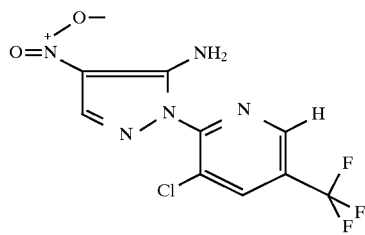

The values in Table 7 clearly demonstrate the advantages of the compound according to the invention. In comparison to comparison compound A, it is selective in the crop soybeans while simultaneously exerting a high herbicidal action.

TABLE 7

Comparison of results from postemergence greenhouse experiments

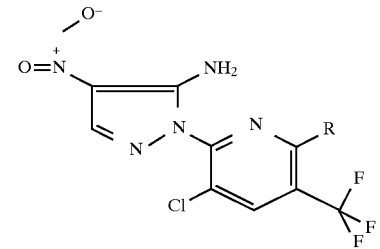

| Ex. No. | | | A | |
| --- | --- | --- | --- | --- |
| R | F | | H | |
| Rate of application (kg of a.i./ha) | 0.0156 | 0.0078 | 0.0156 | 0.0078 |
| Test plants | | Damage in % | | |
| GLXMA | 20 | 20 | 60 | 55 |
| ABUTH | 90 | 90 | 100 | 95 |
| SOLNI | 100 | 100 | 100 | 100 |

We claim:

1. A trifluoromethylpyridine of the formula Ib

where the substituents have the following meanings:

$R^1$ is chlorine or fluorine;

$R^2$ is halogen; and $R^3$ is $C_1$–$C_6$-alkyl, $C_2$–$C_6$-alkenyl or $C_2$–$C_6$-alkynyl, said groups being optionally substituted with 1 to 6 halogen atoms, $C_3$–$C_6$-cycloalkyl which is optionally substituted with 1 to 3 $C_1$–$C_3$-alkyl radicals, $C_1$–$C_6$-cyanoalkyl, $C_1$–$C_4$-alkoxy-$C_2$–$C_6$-alkyl, 3-oxetanyl, carboxyl-$C_1$–$C_6$-alkyl, $C_1$–$C_6$-alkoxycarbonyl-$C_1$–$C_6$-alkyl, $C_1$–$C_4$-alkoxy-$C_2$–$C_4$-alkoxycarbonyl-$C_3$–$C_6$-alkyl, aminocarbonyl-$C_1$–$C_6$-alkyl, $C_1$–$C_4$-alkylaminocarbonyl-$C_1$–$C_6$-alkyl, $C_1$–$C_4$-dialkylaminocarbonyl-$C_1$–$C_6$-alkyl, $C_2$–$C_4$-alkenylaminocarbonyl-$C_1$–$C_6$-alkyl, $C_3$–$C_4$-alkynylaminocarbonyl-$C_1$–$C_6$-alkyl, $C_1$–$C_4$-alkyl-$C_3$–$C_4$-alkenylaminocarbonyl-$C_1$–$C_6$-alkyl, $C_1$–$C_4$-alkyl-$C_3$–$C_4$-alkynylaminocarbonyl-$C_1$–$C_6$-alkyl, $C_3$–$C_6$-(α-alkylalkylidene) iminoxy-$C_2$–$C_6$-alkyl, cyclopropylmethyl, $C_1$–$C_6$-alkylamino, $C_1$–$C_6$-dialkylamino, $C_1$–$C_6$-alkylideneimino or α-($C_1$–$C_4$-alkyl)-$C_2$–$C_6$-alkylideneimino; and halogen is fluorine, chlorine, bromine or iodine.

2. The trifluoromethylpyridine of the formula Ib as defined in claim 1, where $R^1$ is fluorine, $R^2$ is chlorine or fluorine, $R^3$ is $C_1$–$C_4$-alkyl, $C_2$–$C_4$-alkenyl or $C_2$–$C_4$-alkynyl, said groups being optionally substituted with 1 to 6 halogen atoms, $C_3$–$C_6$-cycloalkyl which is optionally substituted with 1 to 3 $C_1$–$C_3$-alkyl radicals, $C_1$–$C_2$-alkoxy-$C_2$–$C_4$-alkoxycarbonyl-$C_1$–$C_4$-alkyl, $C_1$–$C_4$-cyanoalkyl, $C_1$–$C_2$-alkoxy-$C_2$–$C_4$-alkyl, 3-oxetanyl, carboxyl-$C_1$–$C_4$-alkyl, $C_1$–$C_4$-alkoxycarbonyl-$C_1$–$C_4$- alkyl, $C_1$–$C_2$-alkylaminocarbonyl-$C_1$–$C_4$-alkyl, $C_3$–$C_4$-($\alpha$-alkylalkylidene)iminoxy-$C_2$–$C_4$-alkyl, cyclopropylmethyl, $C_1$–$C_4$-alkylamino, $C_1$–$C_4$-dialkylamino, $C_1$–$C_4$-alkylideneimino or $\alpha$-($C_1$–$C_2$-alkyl)-$C_2$–$C_4$-alkylideneimino.

3. The trifluoromethylpyridine of the formula Ib as defined in claim 1 which is 2,5-dichloro-6-methoxy-3-trifluoromethylpyridine.

4. The trifluoromethylpyridine of the formula Ib as defined in claim 1 which is 2-chloro-6-fluoro-2-methoxy-5-trifluoromethylpyridine.

5. The trifluoromethylpyridine of the formula Ib as defined in claim 1 which is 2,5-dichloro-6-propargyloxy-3-trifluoromethylpyridine.

6. The trifluoromethylpyridine of the formula Ib as defined in claim 1 which is 3-chloro-6-fluoro-2-propargyloxy-5-trifluoromethylpyridine.

7. The trifluoromethylpyridine of the formula Ib as defined in claim 1 which is 2,5-dichloro-6-ethoxy-5-trifluoromethylpyridine.

8. The trifluoromethylpyridine of the formula Ib as defined in claim 1 which is 2,5-dichloro-6-n-propoxy-5-trifluoromethylpyridine.

9. The trifluoromethylpyridine of the formula Ib as defined in claim 1 which is 2,5-dichloro-6-isopropoxy-5-trifluoromethylpyridine.

10. The trifluoromethylpyridine of the formula Ib as defined in claim 1 which is 3-chloro-6-fluoro-2-methoxy-5-trifluoromethylpyridine.

11. The trifluoromethylpyridine of the formula Ib as defined in claim 1 which is 3-chloro-2-ethoxy-6-fluoro-5-trifluoromethylpyridine.

* * * * *

UNITED STATES PATENT AND TRADEMARK OFFICE
CERTIFICATE OF CORRECTION

PATENT NO.   : 5,849,920
DATED        : December 15, 1998
INVENTOR(S)  : Hamprecht et al.

It is certified that error appears in the above-identified patent and that said Letters Patent is hereby corrected as shown below:

Column 54,
Line 43, "alkoxycarbonyl-$C_3$-$C_6$-" should be -- alkoxycarbonyl-$C_1$-$C_6$- --.
Line 51, ") iminoxy" should be -- )iminoxy -- (no space between).

Signed and Sealed this

Twenty-fourth Day of December, 2002

JAMES E. ROGAN
*Director of the United States Patent and Trademark Office*